US007214940B2

(12) United States Patent
Cluff et al.

(10) Patent No.: US 7,214,940 B2
(45) Date of Patent: May 8, 2007

(54) APPARATUS AND METHOD FOR INVESTIGATING A SAMPLE

(75) Inventors: Julian Alexander Cluff, Cambridge (GB); Bryan Edward Cole, Cambridge (GB); Donald Dominic Arnone, Cambridge (GB)

(73) Assignee: TeraView Limited (GB)

( * ) Notice: Subject to any disclaimer, the term of this patent is extended or adjusted under 35 U.S.C. 154(b) by 203 days.

(21) Appl. No.: 10/466,398

(22) PCT Filed: Jan. 16, 2002

(86) PCT No.: PCT/GB02/00181

§ 371 (c)(1),
(2), (4) Date: Oct. 30, 2003

(87) PCT Pub. No.: WO02/057750

PCT Pub. Date: Jul. 25, 2002

(65) Prior Publication Data

US 2004/0065832 A1      Apr. 8, 2004

(30) Foreign Application Priority Data

Jan. 16, 2001   (GB)   ................................. 0101120.4

(51) Int. Cl.
*G01J 5/02* (2006.01)
*G01N 23/04* (2006.01)

(52) U.S. Cl. ............................... 250/341.1; 250/341.8; 250/585

(58) Field of Classification Search ............. 250/341.1, 250/341.8, 585
See application file for complete search history.

(56) References Cited

U.S. PATENT DOCUMENTS

| 3,872,315 | A | 3/1975 | Boll |
| 3,936,192 | A | 2/1976 | Skala |
| 4,247,205 | A | 1/1981 | Typpo |
| 4,879,471 | A | 11/1989 | Dahlquist |
| 5,028,790 | A | 7/1991 | McGowan et al. |
| 5,424,836 | A | 6/1995 | Weise et al. |
| 5,467,187 | A | 11/1995 | Beers |
| 5,578,828 | A | 11/1996 | Brown et al. |
| 5,610,713 | A | 3/1997 | Heyn |
| 2003/0226969 | A1* | 12/2003 | Williamson ............... 250/341.1 |

FOREIGN PATENT DOCUMENTS

EP          0 572 798 A2      12/1993

(Continued)

OTHER PUBLICATIONS

Zhiping Jiang et al: "THz imaging via electro-optic effect" Microwave Symposium Digest, 1999 IEEE MTT-S International Anaheim, CA, USA Jun. 13-19, 1999, Piscataway, NJ, USA, IEEE, US, Jun. 13, 1999, pp. 941-944.

(Continued)

*Primary Examiner*—Constantine Hannaher
*Assistant Examiner*—Mindy Vu
(74) *Attorney, Agent, or Firm*—Ostrolenk, Faber, Gerb & Soffen, LLP

(57) ABSTRACT

An apparatus for investigating a sample comprising a source of a beam of radiation, a detector for detecting a beam of radiation reflected by or transmitted through a sample to be imaged, an optical subsystem for manipulating the beam between the source and detector and means for translating the optical subsystem along a first translation axis relative to the source and detector to scan the beam across the sample, wherein the source and the detector are on opposite sides of the subsystem and the beam from the source and the beam reflected or transmitted each enter and exit the subsystem in a direction parallel to the first direction of translation. The apparatus is also suitable for maintaining the relative phase of two beams of radiation, during translation of an optical subsystem.

25 Claims, 12 Drawing Sheets

FOREIGN PATENT DOCUMENTS

| | | |
|---|---|---|
| EP | 0 652 415 A1 | 5/1995 |
| EP | 0 841 548 | 5/1998 |
| EP | 0890862 | 1/1999 |
| GB | 2 126 715 A | 3/1984 |
| GB | 2 128 732 A | 5/1984 |
| GB | 2 204 684 A | 11/1988 |
| JP | 2000-055875 | 2/2000 |
| WO | WO 02/075291 | 9/2002 |

OTHER PUBLICATIONS

Chen Q et al: Near-Field Terahertz Imaging with a Dynamic Aperture Optics Letters, Optical Society of America, Washington, US, vol. 25, No. 15, Aug. 1, 2000, pp. 1122-1124.

Hu B B et al; "*Imaging with Terhertz Waves*" Optics Letters, Optical Society of America, Washington, US, vol. 20, No. 16, Aug. 15, 1995, pp. 1716-1718, 1718A.

* cited by examiner

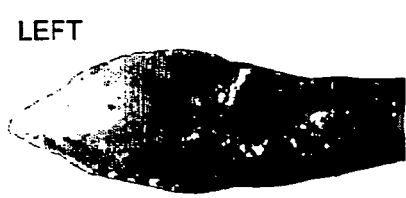
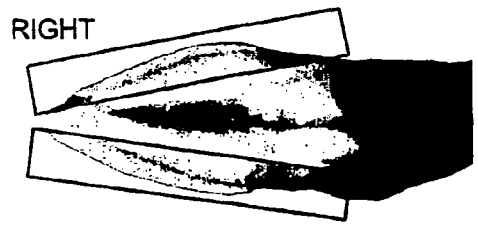
Fig.16a  Fig.16b
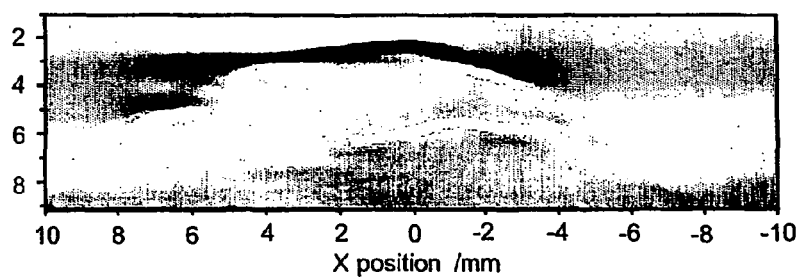
Fig.17a
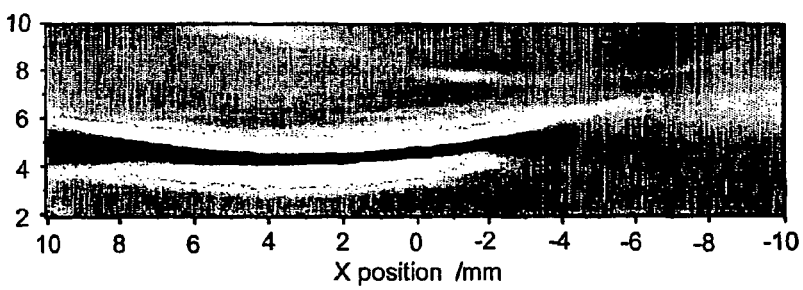
Fig.17b
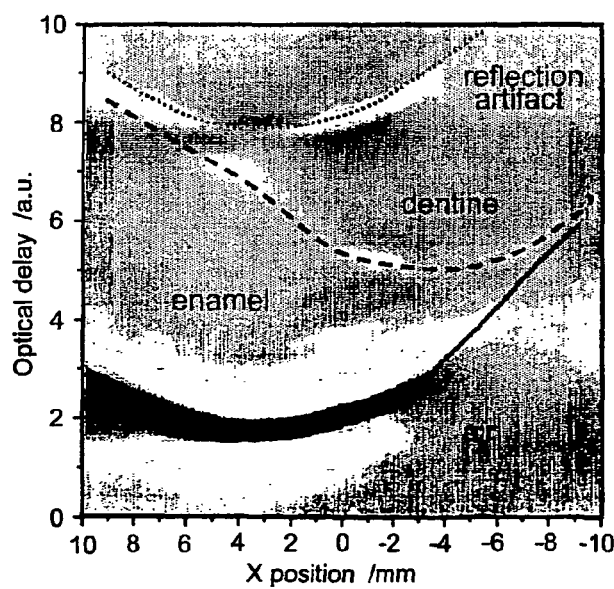
Fig.18

APPARATUS AND METHOD FOR INVESTIGATING A SAMPLE

This invention relates to the field of investigating and imaging samples. More specifically, the invention is concerned with such apparatus which scan a beam of electromagnetic radiation relative to the sample. The present invention is primarily intended for use in the so-called terahertz regime, this is typically thought of as being the range of frequencies from approximately 25 GHz to 100 THz.

It is known to use terahertz radiation to obtain spectra and images of samples. In particular, EP-A-0 727 671 discloses the use of a pulsed beam of terahertz radiation to investigate a sample. The pulsed beam comprises a plurality of different frequency components.

Materials, in general, have a frequency dependent response to radiation. By analysing the frequency components of the terahertz radiation in the time domain or frequency domain, an image of the sample can be generated.

While the present invention is suitable for use to obtain spectra from a number of spatially distinct points on a sample, it is primarily concerned with the production of images of a sample. An image of a sample can be generated by scanning the sample relative to the focus of a beam. In the case of a large sample, it is not practical to move the sample, thus the focus of the beam must be scanned instead.

This has been alluded to in EP-A-0 727 671 which discloses focusing a signal source on distant points and moving the sample or moving the source and detector across the sample. However, no indication is given as to how this may be achieved. Due to the manner of operation of such an imaging system, it is not apparent how the radiation may be scanned over a sample, while still being able to obtain meaningful results. PCT/GB00/00632, by the present applicant, discloses a method and apparatus for imaging a sample using terahertz radiation. The present invention builds on this and offers increased accuracy for imaging.

When considering the problems with scanning the beam relative to the sample it is important to understand what happens when a sample is irradiated by radiation. Electromagnetic radiation is a wave phenomena and hence it is characterised by both amplitude and phase. Thus information regarding the material of the sample, and its internal make-up can be found by measuring the change in amplitude and phase of the radiation introduced by the sample at different frequencies. The phase is related to the propagation path length or propagation time of the radiation.

When the sample is scanned through the beams, the beams and their associated optics do not move, thus it is possible to easily measure the phase change caused by the sample. However, once the beam itself is scanned, problems arise in how to accurately determine the phase shift introduced by the sample.

It is an aim of the present invention to alleviate, or partially mitigate some of the problems associated with the prior art. In particular, it is an aim of the present invention to provide an apparatus which allows scanning of a beam of radiation over a sample in at least one dimension while taking account of any change in time delay introduced by the system itself, so that the delay introduced by the sample may be found.

According to a first aspect of the invention, there is provided an apparatus for investigating a sample, comprising a source of a beam of radiation, a detector for detecting a beam of radiation reflected by or transmitted through the sample, an optical subsystem for manipulating the beam between the source and detector, and means for translating the optical subsystem along a first translation axis relative to a fixed reference point to scan the beam across the sample, wherein the beam from the source enters the subsystem on one side of the subsystem in a direction parallel to the first translation axis, and the beam reflected or transmitted exits the subsystem on the opposite side of the subsystem in a direction parallel to the first translation axis.

The subsystem comprises at least one element for manipulating the beam or pulse of radiation which may be translated along a translation axis relative to sample. Generally, the subsystem will comprise a plurality of elements which may be translated together in unison along the desired translation axis. Preferably, the subsystem will comprise at least one element configured to direct radiation onto the sample and at least one other element configured to direct radiation reflected from the sample into the detector.

The beam enters and exits the subsystem in the same direction and parallel to the axis of translation and the subsystem is moveable along the translation axis. Thus, the path length travelled between the source and detector is constant regardless of the scanning position of the beam. Specifically, if the subsystem is moved away from the source, the extra distance travelled between source and subsystem is compensated by the shortening of the distance travelled between subsystem and detector.

The above arrangement keeps the path length of the irradiating radiation constant regardless of the scanning position of the beam. Thus, providing that the detector is provided with some information concerning the phase of the radiation leaving the source, the phase difference introduced by the sample can be determined.

The detector may be given information about the phase of the radiation leaving the source by a number of different methods. For example, the source and detector may both be provided with a synchronised clock signal; Preferably, a reference beam is used which does not pass through the sample and which has a phase related to that of the beam of irradiating radiation.

In apparatus according to the above aspect of the present invention, the path length of the reference beam will be fixed as the path length of the irradiating radiation is fixed and a known phase between the two beams can be maintained. However, it is also possible to design a system where the path length of the irradiating radiation changes, but where the path length of the reference beam changes by a corresponding amount This arrangement still allows the detector to measure the change in phase between the irradiating beam and reference beam.

Thus, in a second aspect, the present invention provides an apparatus for investigating a sample, comprising a source of a beam of radiation, a source of a reference beam, an optical subsystem for manipulating the source beam means for translating the optical subsystem along a first translation axis relative to the sample to scan the beam across the sample and a detector for detecting the reflected or transmitted beam wherein source and reference beams each enter the subsystem in a direction parallel to the first translation axis.

As the subsystem moves, the relative phase of the source and reference probe as they enter the subsystem will stay the same so that the phase relationship between the two beams is altered only by the source beam impinging on the sample. In this aspect, the reference beam is not stationary relative to the detector, but rather to the source. This allows accounting for the phase change introduced by the apparatus as it moves to be made automatically, and allows a comparison of the source and reference beams at the detector to detect the phase change caused by the delay introduced by the sample. This can be done at many frequencies, the phase change at each frequency not necessarily being the same, due to the frequency dependent refractive index of the sample.

The sample is preferably placed independent of the subsystem so that the sample may remain stationary while the subsystem moves the manipulating elements relative to the sample.

The above description has concentrated on systems which scan in just one direction However, it is possible to put two such systems inside one another in order to scan in two or more directions.

Thus, preferably, a second optical subsystem is provided for manipulating the source beam between the source and the detector, the first subsystem being contained within the second subsystem. Preferably, there are means for translating the second optical subsystem relative to the sample, to scan the source beam across the sample along a second translation axis, wherein the source beam enters the second subsystem in a direction parallel to the direction of translation of the second subsystem.

Preferably, the first and second translation axes are not parallel, so that a focus of the beam may be scanned in two dimensions and a two dimensional image of the sample may be constructed. However, a system where there are two subsystems which scan in the same direction might be useful. For example, the first subsystem may have a limited movement range but have fine control whereas the second subsystem has a much longer movement range, but which cannot be so finely controlled.

The second optical subsystem may be in accordance with the second aspect of the present invention, where the second optical subsystem comprises the detector. The reference beam and source beam entering the second subsystem parallel to a second translation axis relative to the sample.

The detector may be outside the second subsystem in the manner of the first aspect of the present invention. If this is the case then the reference beam and reflected or transmitted beam exit the second subsystem parallel to the direction of translation of the second subsystem. The reference beam and the reflected or transmitted beam both travel the same distance to the detector regardless of the position of the subsystems. Therefore, the phase shift in the reflected or transmitted beam, introduced by the sample, relative to the reference beam is maintained until the beams reach the detector.

The first subsystem which is inside the second subsystem will generally be of the type described with reference to the first aspect of the present invention where the detector lies outside the subsystem.

Preferably the first and second directions of translation are orthogonal. This gives the advantage that the first and second subsystems can move independently, movement along one translation axis not causing any movement along the other translation axis.

However, the first and second translation axes need not be orthogonal for the invention to operate. The beam irradiating the sample may be incident on the sample at any angle, although in general the beam is incident on the sample along a direction largely orthogonal to the first and second translation axes.

It is possible to incorporate first and second subsystems as described above into a third subsystem which moves along a third translational axis. This can be done by arranging the source outside the third subsystem and the source beam, the third subsystem parallel to the third translational axis. The third subsystem would manipulate the beams so as to enter the second subsystem parallel to the second translational axis. In this case, the source and reference beams would each travel the same distance, the change in distance due to movement of the second and third subsystems will be the same for each beam. The apparatus will not introduce any phase difference between the two beams when each subsystem is moved along its translational axis. Alternatively, the source and reference source could be mounted within the third subsystem and moved together along the third translation axis.

The above description has generally referred to systems where the beams of radiation (e.g. the irradiating beam of radiation or the reference beam) pass through free space and are reflected and focused by free space optics. However, the benefits of the first and second aspects of the present invention can also be realised by using flexible waveguides such as optical fibres.

Thus, in a third aspect, the present invention provides an apparatus for investigating a sample is provided, comprising a source of a beam of radiation, a source of a reference beam, an optical subsystem for manipulating the beam between source and detector, and means for translating the subsystem relative to the sample, wherein the reference beam enters the subsystem through an electromagnetic radiation guide, one end of the guide being fixed with respect to the source, the other end of the guide being fixed relative to the subsystem.

This aspect allows for the subsystem to be translated in three dimensions whilst maintaining the path length of the reference beam as it is retained within a guide, one end of which is fixed in relation to the radiation sources, the other end fixed relative to the subsystem. This ensures that the phase relationship between the source and reference beams entering the subsystem is maintained. Preferably, the source is also outside the subsystem and the source beam enters the subsystem through an electromagnetic radiation guide. Preferably, the electromagnetic radiation guides are optical fibres. Any guide may be used which maintains the absolute path of the beams, and which maintains the coherence of the beams.

In apparatus according to any of the above three aspects of the invention, the detector may be a direct detector of THz radiation or it may be of the type which converts THz radiation into an easily readable signal.

For example, the detector may comprise a non-linear crystal which is configured such that upon the radiation of a probe beam and a THz beam, the polarisation of the probe beam is rotated. The probe beam can be of a frequency which can be easily measured (for example near infra-red). Typical crystals which exhibit this effect, the so-called "AC Pockels" effect are GaAs, GaSe, $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium. This type of detection mechanism is generally referred to as 'Electro-optic sampling' or EOS.

Alternatively, the detector could be a so-called photoconducting detector. Here, the detector comprises a photoconductive material such as low temperature grown GaAs, Arsenic implanted GaAs or radiation damaged Si on Sapphire. A pair of electrodes, for example in a bow-tie configuration or in a transmission line configuration are provided on a surface of the photoconductive material. When the photoconductive material is irradiated by the reflected radiation and also, the probe beam, a current is generated between the two electrodes. The magnitude of this photo-voltage current is an indication of the magnitude of the THz signal.

The present invention is primarily intended for use in the THz regime. Although it is possible to generate terahertz radiation directly, the most efficient terahertz generation can generally be achieved by converting an input beam or pump beam into a terahertz beam. Therefore, a frequency conversion member is preferably provided between the source of the pump beam and the sample. This frequency conversion device may be situated anywhere between the source and sample and can be used to irradiate the sample with radiation of a frequency different to that of the pump beam. It is therefore possible to irradiate the sample with radiation frequencies which are not easily directly produced, in a simplified manner.

There are many possible options for the frequency conversion member. For example, the frequency conversion member may comprise a non-linear member, which is configured to emit a beam of emitted radiation in response to irradiation by a pump beam. Preferably, the pump beam comprises at least two frequency components, (or two pump beams having different frequencies are used), the non-linear member can be configured to emit an emitted beam having a frequency which is the difference of the at least two frequencies of the pump beam or beams. Typical non-linear members are: GaAs or Si based semiconductors. More preferably, a crystalline structure is used. The following are further examples of possible materials:

$NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNbsO_{15}$, $AgAsS_3$, proustite, CdSe, $CdGeAs_2$, $AgGaSe_2$, $AgSbS_3$, ZnS, GaSe or organic crystals such as DAST (4-N-methylstilbazolium).

In order to produce an emitted beam having a frequency in the THz regime, preferably the at least two frequencies of the pump beam or beams are in the near infra-red regime. Typically, frequencies between $0.1 \times 10^{12}$ Hz and $5 \times 10^{14}$ Hz are used.

Alternatively the frequency conversion member is a photoconducting emitter, such an emitter comprises a photoconductive material such as low temperature grown or arsenic implanted GaAs or radiation damaged Si or Sapphire.

Electrodes which may be of any shape such as a dipole arrangement, a double dipole arrangement, a bow-tie arrangement or transmission line arrangement are provided on the surface of the photoconductive material. At least two electrodes are provided. Upon application of a bias between the electrodes and irradiation of a pump beam(s) having at least two different frequency components, a beam of radiation is emitted having a frequency different to that of the at least two frequency components of the pump beam or beams.

Preferably, the incident beam is pulsed beam comprising a plurality of frequencies. If a pulse having a plurality of frequencies passes into a sample and onto a detector, the various frequencies will not all arrive at the detector at the same time due to the frequency dependent response of the sample. Thus, a scanning delay line is inserted into the path of either the probe beam or pump beam. By plotting the signal against the delay time (of the scanning delay line), the detected waveform can be measured.

In the above described apparatus, at least part of the apparatus, the optical subsystem, moves relative to the sample. In order to achieve this, the apparatus preferably further comprises mounting means which are used to mount the sample. In some situations, it will be advantageous to provide a member which is substantially transparent to the radiation of interest, in this THz radiation for the sample to be sit upon. Thus, the radiation must pass through this member in order to irradiate the sample. This member can potentially give rise to internal reflections. Therefore, there is a need to try and at least partially remove reflections due to the member.

In a fourth aspect, the present invention provides a method of investigating a sample, a method comprising:
(a) irradiating a sample with an irradiating beam of radiation, through a member which is substantially transparent to the beam of radiation;
(b) detecting the radiation reflected from the sample;
(c) irradiating the said member in the absence of the sample; and
(d) detecting radiation reflected from the member during step (c);
(e) subtracting the signal measured by the detector during step (d) from the signal measured by the detector during step (b).

Steps (a) and (b) can be continually repeated during a scanning operation and the same signal measured in step (d) can be used regardless of the current scanning position.

Steps (c) and (e) generally referred to as measuring the "base line" signal and the above method is generally termed base line subtraction. The base line signal can be measured before or after scanning the sample. For example, if the system is used to measure a plurality of samples, then the base line signal only needs to be measured once. Generally, the above system will be used during pulsed imaging where the beam of radiation comprises a plurality of frequencies.

The method of subtracting the signal due to the window from the sample can be performed in the time or frequency domain.

In a fifth aspect, the present invention provides an apparatus, the apparatus comprising an emitter for emitting a beam of radiation to irradiate the sample; a detector for detecting radiation reflected from the sample; a member, which is substantially transparent to radiation, located between the sample and the emitter and detector; means for subtracting a predetermined signal detected by the detector from a further signal detected by the detector.

It may also be desirable to measure a reference signal and divide the signal measured in step (b) by this reference signal. For example, this reference signal could be obtained by replacing the sample with a known reference, for example a silver mirror.

The baseline signal can be subtracted from both the sample signal and also the reference signal. Alternatively, the baseline and reference signals can change roles and the reference signal can be subtracted from both the sample signal and the baseline signal, the reference subtracted sample signal being divided by the reference subtracted baseline signal. Signals may be subtracted from one another in the time or the frequency domain. Division of any signals should be performed in the frequency domain The obtained THz signal regardless of whether or not it has been subjected to baseline subtraction or division by a reference signal is preferably filtered.

Thus, in a sixth aspect, the present invention provides method of investigating a sample, the method comprising the steps of:
(a) irradiating a sample with a beam of pulsed radiation comprising a plurality of frequencies;

(b) measuring the beam reflected by or transmitted through the sample and obtaining a signal representative of the measured beam;

(c) multiplying the signal of step (b) in the frequency domain by the complex Fourier transform of function F(t), wherein F(t) is a non-zero function whose integral between time limits $t_1$ and $t_2$ is zero, where $t_1$ and $t_2$ are chosen on the basis of the time delay introduced by the sample.

To clarify, the sample will introduce a time delay into the path of the beam. Considering the case of transmission, if the sample has the same properties as free space, then the radiation will pass through the sample without any delay. However, if the sample (as it almost certainly will) introduces a time delay into the beam, then $t_1$ will be set to a negative value which has a magnitude is equal to or larger than the expected value of this time delay. $t_2$ will generally, be set to the positive value of $t_1$.

Similarly, during reflection, $t_1$ will be set to a negative value which has a magnitude is equal to or larger than the expected value of this time delay introduced by the pulse being reflected from the deepest point of interest in the sample. $t_2$ will generally, be set to the positive value of $t_1$.

Generally, the method of the above aspect of the present invention will be performed using the above described apparatus where the radiation is measured using a reference beam and wherein a scanning delay line is introduced into the path of the reference beam or irradiating beam in order to measure the phase change introduced by the sample. In this situation, $t_1$ and $t_2$ will be the negative and positive limits of the scanning delay line. These may be set to the duration of the pulse or possibly a shorter time range.

Preferably function F(t) comprises a Gaussian component Generally, $t_1$ and $t_2$ are symmetric about 0, preferably F(t) is also symmetric about zero.

As the signal is usually digitally sampled, strictly a summation is performed as opposed to an integral.

A particularly preferable form of F(t) is provided by:

$$F(t) = \frac{2}{\pi} \left\{ \frac{e^{-2\left(\frac{t}{\alpha}\right)^2}}{\alpha} - \frac{e^{-2\left(\frac{t}{\beta}\right)^2}}{\beta} \right\}$$

where $\alpha$ and $\beta$ are constants.

Preferable $\alpha$ is substantially equal to the shortest pulse length of the beam of pulsed radiation and $\beta$ is set to be much longer than the pulse length, typically 5 to 100 times the pulse length. However, both of these values will generally be optimised by the operator.

If $\beta$ is greater than or comparable to the time which it takes the radiation to penetrate the sample to the point of interest then, F(t) can take the simplified form:

$$F(t) = \frac{2}{\pi} \left\{ \frac{e^{-2\left(\frac{t}{\alpha}\right)^2}}{\alpha} - \frac{1}{T} \right\}$$

where $\alpha$ is a constant which is substantially equal to the shortest pulse length of the beam and T is substantially equal to the time which it takes the beam of radiation to penetrate to the deepest point of interest in the sample.

Preferably data which has been baseline subtracted is filtered. Thus, preferably, step (b) comprises:
 (b(i)) irradiating a sample with a beam of radiation, through a member which is substantially transparent to the beam of radiation;
 (b(ii)) detecting the radiation reflected from the sample;
 (b(iii)) irradiating the said member in the absence of the sample; and
 (b(iv)) detecting radiation reflected from the member during step (b(iii));
 (b(v)) subtracting the signal measured by the detector during step (b(iv)) from the signal measured by the detector during step (b(ii)).

The data has also been preferably divided by a reference signal before filtering. Thus, step (b) may comprise:
 (b(i)) irradiating the sample with a beam of radiation, through a member which is substantially transparent to the beam of radiation;
 (b(ii)) detecting radiation which is transmitted through or reflected from the sample;
 (b(iii)) irradiating the said member in the presence of a reference sample having known reflection and/or transmission characteristics; and
 (b(iv)) detecting radiation which is reflected from or transmitted through the reference sample during step (b(iii));
 (b(v)) dividing the signal measured by the detector during step (b(ii)) with the signal measured by the detector during step (b(iv)).

More preferably the signal has been baseline subtracted and divided by a reference signal prior to filtering. Thus step (b) may comprise:
 (b(i)) irradiating the sample with a beam of radiation, through a member which is substantially transparent to the beam of radiation;
 (b(ii)) detecting radiation which is transmitted through or reflected from the sample;
 (b(iii)) irradiating the said member in the presence of a reference sample having known reflection and/or transmission characteristics; and
 (b(iv)) detecting radiation which is reflected from or transmitted through the reference sample during step (b(iii));
 (b(v)) irradiating the said member in the absence of the sample;
 (b(vi)) detecting radiation reflected from the member during step (b(v));
 (b(vii)) subtracting the signal measured by the detector during step (b(vi)) from the signal measured by the detector during step (b(ii));
 (b(viii)) subtracting the signal measured by the detector during step (b(vi)) from the signal measured by the detector during step (b(iv));
 (b(ix)) dividing the signal obtained in step (b(vii)) with the signal obtained in step (b(viii)).

As explained above, the reference signal and the baseline signal are interchangeable, thus, step (b) may comprise:
 (b(i)) irradiating the sample with a beam of radiation, through a member which is substantially transparent to the beam of radiation;
 (b(ii)) detecting radiation which is transmitted through or reflected from the sample;
 (b(iii)) irradiating the said member in the presence of a reference sample having known reflection and/or transmission characteristics; and (b(iv)) detecting radiation which is reflected from or transmitted through the reference sample during step (b(iii));

(b(v)) irradiating the said member in the absence of the sample;

(b(vi)) detecting radiation reflected from the member during step (b(v));

(b(vii)) subtracting the signal measured by the detector during step (b(iv)) from the signal measured by the detector during step (b(ii));

(b(viii)) subtracting the signal measured by the detector during step (b(iv)) from the signal measured by the detector during step (b(vi));

(b(ix)) dividing the signal obtained in step(b(vii)) with the signal obtained in step (b(viii)).

Unwanted artefacts in the image may also be removed by appropriate choice of the thickness of the emitter or detector such that artefacts due to internal reflection within the emitter or detector occur at longer delay times than those of interest in the sample.

Thus, in a seventh aspect, the present invention provides an apparatus for investigating a sample with a beam of radiation, the apparatus comprising an optically active element for irradiating the sample and/or detecting radiation reflected from the sample, the optically active element having at least two interfaces, the distance between the interfaces being great enough such that the beam of radiation takes longer to travel between the interfaces than it does to travel from the surface of the sample to the deepest point of interest within the sample.

The optically active element can be an emitter, detector or transceiver.

The apparatus may comprise two optically active elements, where the first optically active element is configured as an emitter and the second as a detector, wherein the second optically active element comprises at least two interfaces, the distance between the interfaces being great enough such that the beam of radiation takes longer to travel between the interfaces than it does to travel from the surface of the sample to the deepest point of interest within the sample.

The optically active element may be configured as an emitter which emits the beam of radiation having the desired frequencies in response to irradiation by at least one input beam having a different frequency. Such an emitter may comprise an optically non-linear material or a photo-conductive material.

The optically active element may be configured as a detector which detects the beam of radiation having the desired frequencies using at least one probe beam having a different frequency to that of the beam of radiation. Such a detector may comprise an optically non-linear material which is configured to alter the polarisation of the probe beam in response to irradiation with the beam of radiation or a photoconductive material which is configured to generate a current within the photoconductive material in response to irradiation with both the beam of radiation and the probe beam.

The present invention will now be described with reference to following non-limiting embodiments, in which:

FIGS. 16a and 16b show visible images of a human incisor, FIG. 16a shows the outside image whereas 16b shows the inside side image, front and back faces are identified in FIG. 16b;

FIGS. 17a and 17b show THz images of the from and back faces identified in FIG. 16b; and FIG. 18 shows a THz image of a tooth indicating the enamel air and enamel dentine interfaces.

Figure 1:
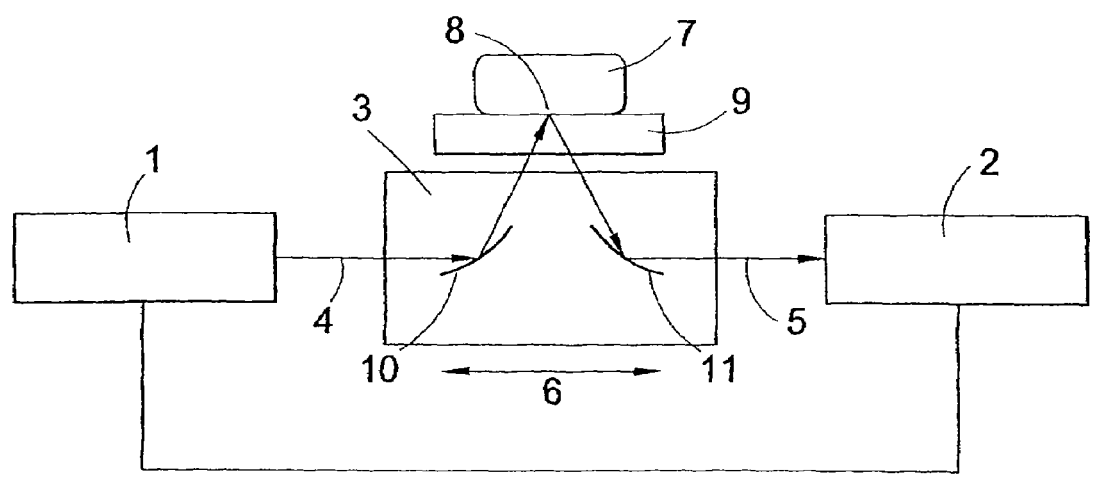
FIG. 1 is a schematic diagram of an imaging apparatus forming a first embodiment of the present invention.

FIG. 1 shows schematically an apparatus according to the invention The apparatus comprises a source 1, detector 2, a subsystem 3 containing focusing optics 10, 11 and a substantially transparent mounting means 9 for sample 7.

In this embodiment, the source 1 and detector 2 are provided on opposite sides of the subsystem 3. The source 1 provides abeam of irradiating radiation 4 which is directed by the optics 10, 11 in optical subsystem 3 onto sample 7. The irradiating radiation is then reflected 5 back into subsystem 3 and the beam of reflected radiation 5 is then directed into detector 2.

The subsystem 3 is translatable along a translation axis 6 and the source beam 4 and reflected radiation beam 5 are parallel to this translation axis 6, as they respectively enter and exit subsystem 3.

The subsystem 3 includes a first parabolic mirror 10 which reflects and focuses the source beam 4 to a focus 8 outside the subsystem 3. Ideally, the focus 8 is configured such that it is at the point of interest of the sample 7. The subsystem also comprises second parabolic mirror 11, which directs the beam of reflected radiation 5 to exit the subsystem 3 parallel to the translation axis 6 and into detector 2.

Although parabolic mirrors are used as the optics which direct radiation to and from the sample 7, it is possible to use other optics which will focus and/or reflect the source and reflected beams 4, 5 in the required manner.

The sample 7 is placed on mounting means 9 which remain fixed with respect to both the source 1 and the detector 2. The mounting means in this particular example is a fixed window which allows the transmission of the beam of irradiating radiation 4 and the reflected radiation 5. The sample is provided on the opposing side of the window 9 to the optical subsystem 3.

As the subsystem 3 moves along the translation axis 6 it causes the focus 8 in the beam 4, 5 to be scanned across the sample 7.

The above apparatus ensures that the path length travelled by the beam 4, 5 remains constant, regardless of the position of the subsystem 3 along the translation axis 6. Thus phase of the beam 4, 5 is not affected by the movement of the subsystem 3 along the x translation axis 6 in the absence of the sample.

In order to derive sensible information from the sample 7, there is a need to measure the change in the phase of the source beam 4 caused by the sample 7. Thus, detector 2 needs to know some information about the phase of the radiation leaving the source 1 The dotted line indicates that such information is required. A way of doing this is to use a reference beam (not shown) which has a phase related to that of the source beam 4 and which is received by the detector. Actually many detectors of THz radiation require a reference beam in order to detect radiation received by the detector. Such detectors will be described in more detail later.

In the apparatus of FIG. 1 the path length between the source and the detector remains the same, thus a reference beam having a known path length can be provided to the detector 2. The use of a reference beam will be described in great detail with reference to FIG. 3.

Figure 2:
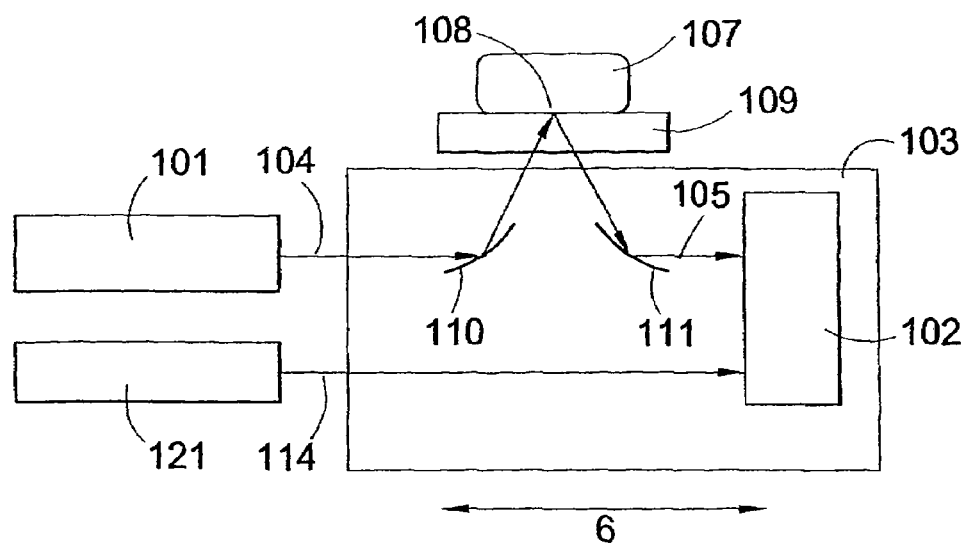
FIG. 2 is a schematic diagram of an imaging apparatus forming a second embodiment of the present invention.

FIG. 2 shows, schematically, a second embodiment of the invention. However, in this case, two sources of radiation 101, 114 are provided, one for the source beam 104 and the other 114 for the reference or probe beam 104 for the detector 102. The detector 102 is provided within the optical subsystem 103 and moves with the optical subsystem. The apparatus is configured such that movement of the detector 102 causes the same change in the path length of the source beam and the reference beam, thus preserving the phase relationship between the two beams.

A first source 101 emits a source beam 104 and a detector 102 detects the beam of reflected radiation 105 after it has been reflected from sample 107. A subsystem 103 is movable along translation axis 106. The source beam 104 is parallel to the translation axis 106 when it enters the subsystem 103. The detector 102 is placed within the subsystem 103. A reference source 121 provides a reference beam 114 which enters the subsystem 103 parallel to both the source beam 104 and translation axis of the subsystem 103 and is also detected by the detector 102.

The subsystem 103 includes a parabolic mirror 110 which reflects and focuses the source beam 104 to a focus 108 outside the subsystem 103. The subsystem 103 also includes a further parabolic mirror 111, which collects reflected radiation from the sample 107 and directs it to the detector 102. Other optical elements could be used instead of parabolic mirrors.

Sample 107 is placed on mounting means 109, which remains fixed with respect to both the source 101 and the reference source 121. As the subsystem 103 moves along the translation direction 106 the focus 108 of the source beam 104 is scanned across the sample 107.

The apparatus of FIG. 2 ensures that the phase difference between the source beam 104 and the reference beam 114 remains constant as they enter the subsystem regardless of the movement of the subsystem 103 along the translation axis 106. This is because any change in the path length of the source beam 104 from the source to its entry to the subsystem 103 due to the movement of the subsystem 103 along the translation axis 106 is the same as the change in the path length of the reference beam 114 from the reference source 121 to its entry to the subsystem 103.

In both the above embodiments, the source 1, 101 is a source of coherent radiation, for example a laser, and more particularly a mode locked Ti:Sapphire laser may be used to produce near infrared radiation. The apparatus of the present invention is primarily intended for use with THz radiation. Although dedicated sources of THz radiation exist, generally, THz radiation is produce using a frequency conversion member, such as a non-linear crystal which is configured to generate THz radiation in response to irradiation by an input beam having a frequency different to that of the THz radiation or a photoconductive material which is configured to emit THz radiation upon application of a bias and irradiation by a input beam having a different frequency to that of the THz radiation.

The source beam may be used directly or it may be passed through such a frequency conversion member. The part of the source beam which is incident on the frequency conversion member will be referred to as the pump beam and the part of the source beam emitted from the frequency conversion member will be referred to as the THz beam. Although this invention is primarily intended for use in the THz regime, other frequencies could also be used.

The frequency conversion member may be driven by using a pump beam comprising pulsed infra-red radiation which excites the member to produce a single cycle terahertz pulse centred at round 1 THz, the spectrum being broad due to the short pulse length, while maintaining the phase characteristics from the near infrared pulse. The frequency conversion member may be placed in the path of the source beam either inside the optical subsystem or outside the optical subsystem 3, 103.

The parabolic mirror 10, 110 used to focus the source beam 4, 104 is used to a small focus 8, 108, typically less than from 1 mm while ensuring that radiation from across the whole cross section of the beam 4, 104 arrives at the focus 8, 108 substantially simultaneously. A simple off axis parabolic mirror may be used for near infrared radiation or terahertz radiation. No specialised optical equipment is required for the manipulation of the terahertz pulses i.e. optical equipment which is suitable for infrared radiation manipulation may be used The detector 2, 102 may be any detector suitable for detecting the frequency of radiation supplied by the source 1, 101 and any reference source 121. For example, in the case where the source 1, 101 is a terahertz frequency beam having a range of frequencies centred around 1 THz, and a reference source 121 is supplied and is a near infrared beam, for example at a frequency of $1 \times 10^{14}$ Hz, the detector may be either a non-linear crystal or a photo-conducting device. These are described in greater detail in the embodiments relating to FIGS. 3 and 5 below.

In the embodiment of FIG. 2, the reference source 121 is a source of coherent radiation, but is not necessarily of the same frequency as the source 101. A common source can be used for the source beam 104 and reference beam so that they are in phase.

A beam splitter (discussed in further embodiments) such as a semi-transparent mirror, or a prism, is used to split the beam to produce the source beam 104 and reference beam 114.

The mounting means may be made out of any material substantially transparent to the radiation being used at the focus 8, 108. In the case of a terahertz frequency apparatus, the mounting means is a crystal quartz window. It is possible that the mounting means 9, 109 has a hole through it such that radiation can reach the sample 7, 107 from the optical subsystem 3, 103.

The movement of the subsystem 3, 103 may be by any conventional means (not shown). For example, a stepper motor and/or rack & pinion system (not shown) may be employed. This allows accuracy of displacement and enables the position of the subsystem 3, 103 to be known by a controlling system (not shown). Thus the position of the focus 8, 108 can be determined with a high degree of accuracy. Typically, an accuracy of position of 0.01 mm is sufficient for the subsystem 3, 103, when terahertz radiation is used to irradiate the sample 7, 107.

Figure 3:
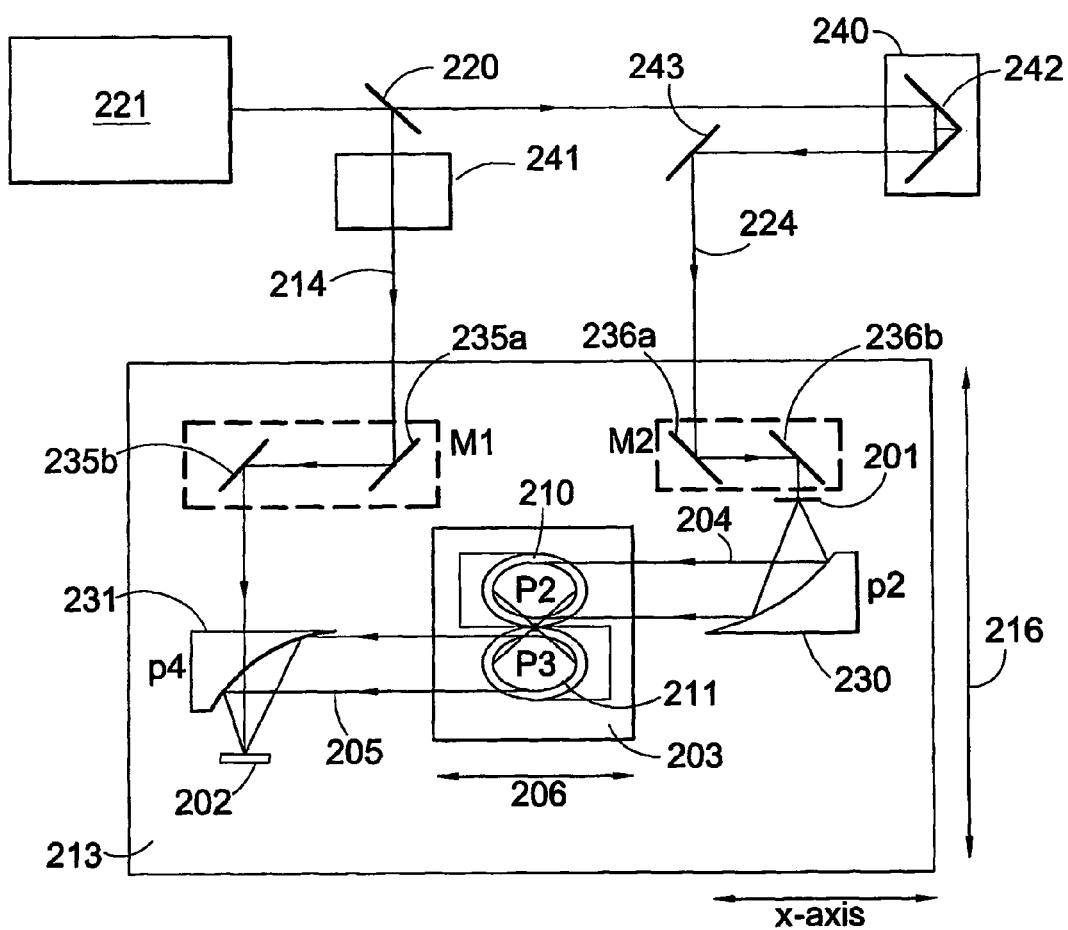
FIG. 3 is a schematic diagram showing an apparatus in accordance with a third embodiment of the present invention.

A third embodiment of the present invention will now be described with reference to FIG. 3. The apparatus of FIG. 3 allows a sample to be scanned in two orthogonal directions. For the purposes of this example, the two directions will be the x direction and y direction. The apparatus uses a x optical subsystem (similar to that described with reference to FIG. 1) placed within a y optical subsystem (similar to that described with reference to FIG. 2).

Source 221 comprises a mode locked laser generating sub 200 fs pulses in the near infrared spectral range (approx. $1 \times 10^{14}$ Hz). Specifically, a Cr:LiSAF laser (100 MHz, 100 fs and 100 mW) is used. Other sources can be used, for example, a mode locked Ti:Sapphire laser. These pulses of near infrared radiation are split using a beam splitter 220, into a pump pulse 224, and a reference pulse or probe pulse, 214.

The pump pulse 224 travels through scanning optical delay line 240, which introduces an oscillating delay into the pump pulse 224. The scanning delay line comprises a retro reflection mirror 242 which reflects the pump beam back on itself and onto planar mirror 243. Mirror 243 is configured to reflect the beam out of the scanning delay line 240 at right angles to itself and into the y optical subsystem 213 parallel to the translation axis. By moving the retroreflector 242 back and forth parallel to the direction on the pump beam, the optical path length is oscillated.

The irradiating radiation 224 then enters the y subsystem 213 parallel to the translation direction 216 of the y subsystem 213. On entering the y subsystem 213, the pump beam 224 is reflected through 90° by mirror 236a and then through a further 90° by mirror 236b such that the path of the pump beam 224 is parallel to the direction which it entered subsystem 213. Mirrors 236a and 236b serve to direct the pump beam 224 onto frequency conversion member 201 which converts the near infrared pump beam 224 into a beam of THz radiation 204.

Frequency conversion member 201 may comprise a non-linear crystal. If a non-linear crystal is irradiated by two different frequencies $\omega_1$ and $\omega_2$, radiation having a frequency which is the difference or the sum of these frequencies is outputted. Preferably, the pump beam and crystal is chosen such that the crystal outputs radiation having a frequency which is the difference of the two frequencies impinging on the crystal.

As the frequency conversion member 201 is irradiated with infrared radiation $\omega_1$ and $\omega_2$, the electrons vibrate to emit radiation with a THz frequency, the THz radiation $\omega_{THz}=\omega_1-\omega_2$.

Often, such a frequency conversion member 201 will have phase matching means in order to keep the transmitted THz signal and the incident radiation in phase as they pass through the frequency conversion member 201. (For example, see GB 2 343 964. Such phase matching can be achieved by providing the frequency conversion member 201 with a variation in its refractive index configured to keep the two signals in phase (at all points) as they pass through the frequency conversion member 201.

The frequency conversion member 201 may also be a so-called photoconducting emitter comprising a photoconducting material such as low temperature grown GaAs or radiation damaged Si on Sapphire. A pair of electrodes are formed on a surface of the photoconducting material. THz radiation will be emitted having a frequency (or frequencies) which is the difference in the frequencies of the photoconducting material with the pump beam and upon application of a bias between the two electrodes. (For further details on photoconductive emitters see U.S. Pat. No. 5,729,017).

The terahertz beam pulse 204, produced by the frequency conversion member 201, is collimated using one or more parabolic mirrors 230, which are suitable for use with terahertz frequency radiation. Parabolic mirror 230 serves to direct the radiation parallel to the x translation axis 206 and to maintain the phase of the THz radiation across its cross section. The incident THz pulse 204 then enters the x subsystem 203 collimated and parallel to the x translation axis 206.

The x subsystem 203 performs in a similar manner to that described in the first embodiment and comprises a set of elements for manipulating the pulse of radiation 204, 205 between its to entry and exit from the x subsystem 203. The x subsystem can move along the x-translation axis.

The x subsystem 203 comprises a first parabolic minor 210, which focuses the THz beam 204 to a focus (not shown) outside the x and y subsystems 203, 213.

The sample (not shown) is placed on mounting means (not shown) which remain fixed along the x translation axis 206 with respect to both the frequency conversion device 201 and the detector 202, and fixed in the y translation axis 216 with respect to the source 221 such that the beam can be scanned along the x and y axes of the sample.

The pulse 204 is incident on the sample (not shown) in a direction largely orthogonal to the x and y translation axes 206, 216. However, it is possible to arrange the pulse 204 to be incident on the sample 207 at any angle. Radiation reflected by the sample is collected by y parabolic mirror 211 and is collimated parallel to the x translation axis 206 of the subsystem 203. The reflected THz radiation 205 exits the x subsystem 203 in the same direction as the incident pulse 204 and on the opposite side of the x subsystem 203.

The reflected THz radiation 205 which exits the x subsystem 203 back to the y subsystem where it is collected by parabolic mirror 231 and directed onto detector 202. Probe beam 214 is also incident on detector 202.

Probe beam 214 from beam splitter 220 is directed though fixed delay line 241 and into the y subsystem 213. The probe beam 214 and THz beam 205 need to reach the detector 202 in phase with one another. A scanning delay line 240 is placed in the path of the pump beam 224 in order to scan the phase of the pump beam in order to measure the phase changes caused by the sample. A fixed delay 241 is also included in the reference beam 214 in order to ensure that the probe and reflected THz beams can be brought into phase at detector 202. In order to allow translation of the y subsystem 213 along a y translation axis 216, the pulses 214, 224 enter the y subsystem 213 parallel to this y translation axis 216, and preferably are collimated.

The difference in path length between the probe 214 and pump 224 beams remains the same regardless of the position of the y subsystem 213 along the y translation axis 216 so that the phase relationship between the probe and pulse beams is maintained.

Once the probe beam 214 enters the y subsystem, it is reflected through 90° by first planar mirror 235a and it is then reflected though a further 90° by second planar mirror 235b such that the probe beam 214 is still travelling parallel to the y translation axis. Mirror 235b serves to direct the probe beam through a hole in parabolic mirror 231 such that the probe beam can be combined with the radiation reflected from the sample for detection.

As the parabolic mirror 230 is arranged so that the terahertz pulse 204 enters the x subsystem 203 collimated and parallel to the x translation axis 206, and parabolic mirror 211 causes the pulse to be collimated and parallel to the x translation axis as it leaves the x subsystem 203, this allows the x subsystem 203 to be moved along the x translation axis without varying the total path length travelled by the terahertz radiation 204, and reflected/transmitted radiation 205. Hence no phase change in the pulse is introduced at the detector 202 by virtue of the movement of the x subsystem 203 along the x translation axis 206.

The y subsystem 213 is translatable along the y translation axis 216, carrying the x subsystem 203 with it. The x subsystem 203 is within the y subsystem 213 so that the x subsystem 203 may still be translated along the x translation axis 206, while the y subsection 213 is translated along the y translation axis 213.

The detector is of the photoconducting type, comprising a photoconductive detection member which may be, for example, GaAs, radiation damaged Si on Sapphire etc. The THz radiation is incident on a first surface of the photoconductor 202. A pair of electrodes (not shown) are located on the photoconductor 202 on the first surface.

The probe beam 214 illuminates the surface of the detector between the electrodes. The reflected Terahertz radiation 205 which is collected by the lens induces a photocurrent through the region between the electrodes which is being illuminated by the probe beam 214. The current, which can be detected by the electrodes, is proportional to the strength of the THz field. The current is generated when the THz radiation arrives at the detector 202 in phase with the probe beam.

The travel of the terahertz radiation pulse in the sample (not shown) will induce a delay in the pulse. This delay will depend upon how far into the sample 207 the pulse travels before being reflected, or otherwise directed back to the parabolic mirror 211. It will also depend on the refractive index of the sample at each frequency within the pulse. The pulse 205 is therefore broken up into different temporal elements by travelling through the sample, these different elements arriving at the detector at different times. These elements are compared with the reference pulse.

However, all frequencies of the reference pulse arrive at the same time. In order to overcome this, the scanning time delay is used to introduce a time delay in either the pump pulse or the probe pulse, (in this case, the pump pulse), so that it can be compared to parts of the pump pulse with different time delays. Therefore, it is possible to detect the delay introduced due to the sample at different frequencies, and the extent of the delay will give an indication of how far into a sample the pulse travelled at that frequency.

Also, because of the different reflectivities and absorption characteristics for different frequencies of terahertz radiation for a given sample, an indication of the material contained within a sample at various depths can be obtained. Since reflection of radiation will occur at a boundary between two materials with different optical characteristics, an indication of the depth or thickness of, for example, a surface layer may be determined.

Additionally, when the y subsystem 213 is translated along the y translation axis 216, the change in path length of each of the pump 224 and probe 214 pulses is the same. Although the probe beam 214 does not travel the along the same optical path as the pump pulse for irradiating the sample, any changes to the sample path length are kept the same as those to the probe path length by the arrangement so that a comparison of the phase of the two is possible, the only phase change which will be introduced between the two pulses will be due to the sample 207.

The y translation axis 216 is orthogonal to the x translation axis 206 so that independent movement in two dimensions of an orthogonal co-ordinate system is possible. Although the terms 'x' axis and 'y' axis have been used, the subsystems could be configured to move along any two axis regardless of whether or not they are orthogonal or non-orthogonal.

Although the above description has discussed reflecting radiation from the sample, to image the sample. In such an arrangement, the sample (not shown) is placed off axis from the parabolic mirrors 210, 211. However, transmission measurements are also possible if the sample is placed between the parabolic mirrors 210, 211. Other focusing elements could be used in addition to or instead of parabolic mirrors.

Figure 4:
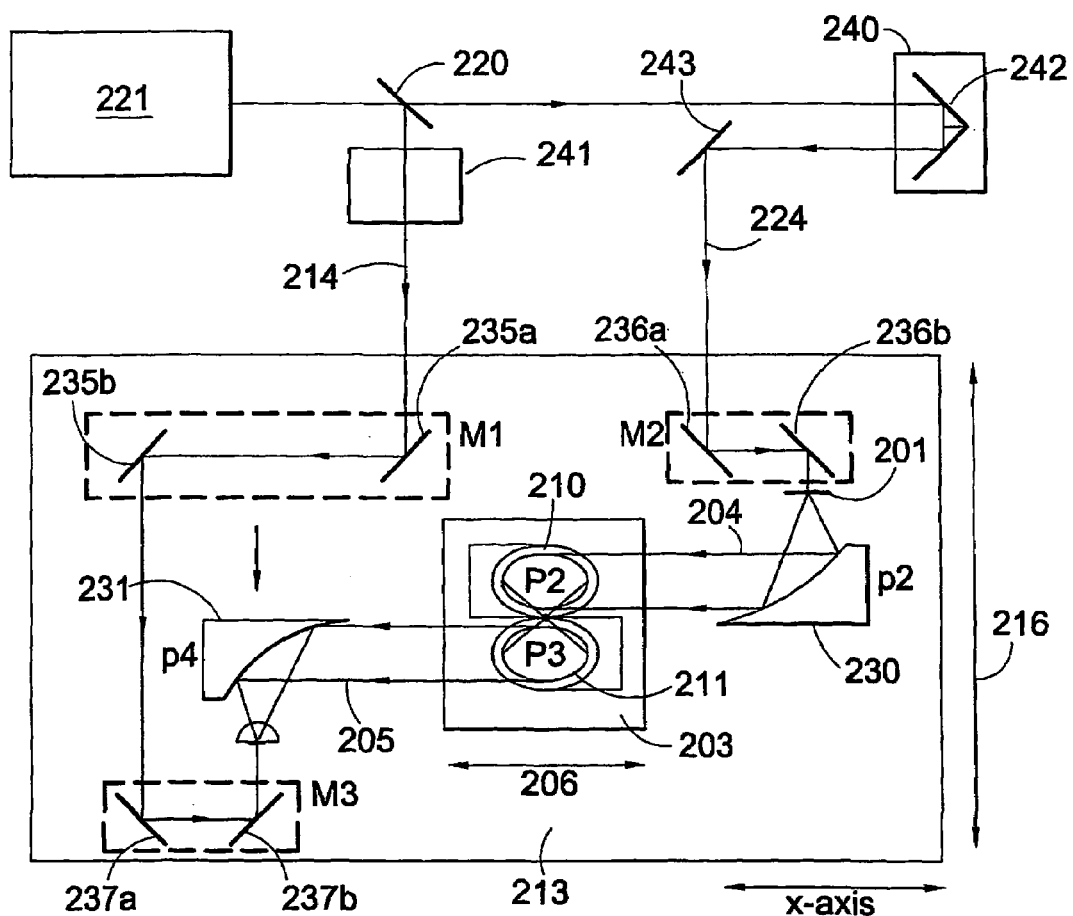
FIG. 4 is a schematic diagram showing an apparatus in accordance with a fourth embodiment of the present invention.

FIG. 4, shows schematically a fourth embodiment which is similar to the third embodiment. However, in this embodiment, the reflected radiation and the probe pulse are incident on opposing sides of the detector 202.

To avoid unnecessary repetition, like reference numerals will be used to denote like features. Probe pulse 214 enters the y subsystem parallel to the y translation axis and is reflected using mirrors 235a and 235b which direct the probe beam 214 parallel to the y translation axis. The probe beam then impinges on planar mirror 237a which rotates the probe beam through 90° and onto mirror 237b. Mirror 237b reflects the beam through a further 90° such that the beam is reflected back parallel to its original path and onto the front of detector 202.

The path of the pump beam and reflected THz beam 205 remains identical to that previously described with reference to FIG. 3.

The reflected THz radiation 205 from the sample is incident on the back surface of the detector 202 and is collected by lens 242, which may be hemispherical or have another shape. The lens is provided on the back surface of detector 202.

On the opposing side of the detector 202 a pair of electrodes (not shown) is located. The probe beam 214 is incident on this side of the detector 202 to the side of the detector which receives the reflected THz beam 205.

Alternatively, they may be triangular and arranged in the shape of a bow-tie to from a so-called bow-tie antenna. They may also be interdigitated electrodes at the centre of a bow-tie or spiral antenna. A transmission line arrangement of electrodes such as that disclosed in Fattinger et al Appl. Phys. Lett. 54 4901 (1989) may also be used.

Figure 5:
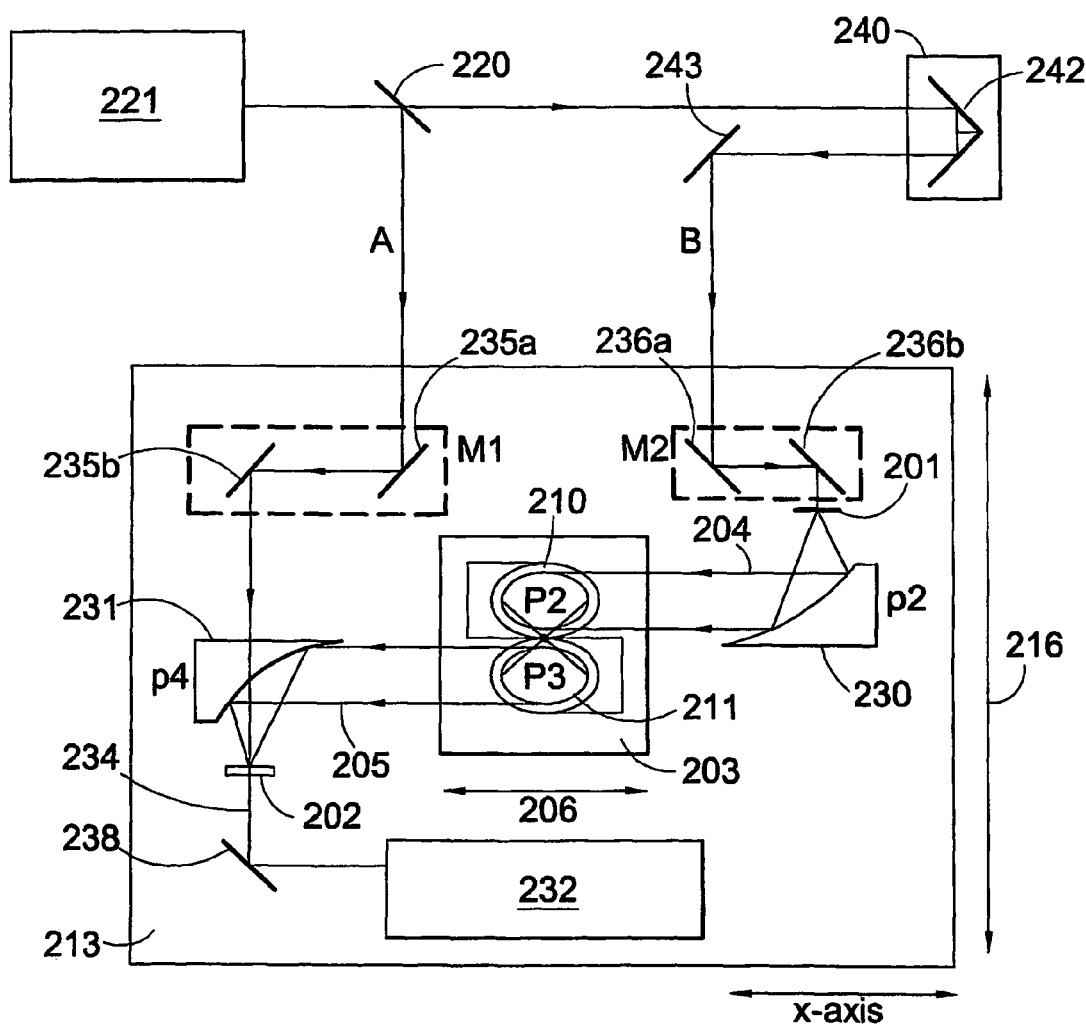
FIG. 5 is a schematic diagram showing an apparatus in accordance with a fifth embodiment of the present invention.

FIG. 5 shows schematically a fifth embodiment of the invention. This embodiment functions in largely the same manner as the embodiment of FIG. 3 However, in FIG. 5, the detector 202 is replaced by a non-linear crystal which is configured to operate as an electro-optic sampling (EOS) mixing crystal. To avoid unnecessary repetition, like reference numerals have been used to denote like features.

In this embodiment, the probe pulse 214 and the reflected terahertz pulse from the sample (not shown) are both incident on the detector 202 on the same side in the same manner as described with reference to FIG. 3. The EOS mixing crystal 202 is not the final detection means, but instead the EOS mixing crystal encodes information from terahertz pulse 205 onto the probe pulse 214 by way of altering the polarising of the probe pulse 214 as it passes through the EOS mixing crystal 202. In order for this to happen, the probe pulse 214 must arrive at the detector 202 in phase path the reflected THz radiation 205.

An EOS mixing crystal 202 utilises the physical phenomenon known as the AC Pockels effect. The transmitted THz radiation 205 from the sample (not shown) is detected by passing the probe beam 214 through the crystal 202 with the reflected THz pulse 205. The reflected THz pulse 205 modulates the birefringence of the detection crystal by the AC Pockels effect.

Prior to entry into the crystal 202, the THz pulse 205 and the probe pulse 214 are polarised. Where there is no THz pulse 205, the probe pulse 214 passes unaffected through the EOS mixing crystal 202. When the probe pulse 214 exits the mixing crystal, it is passed into a polarisation detection system 232.

The details of the polarisation detection system are not shown as they well known, see for example GB 2 343 964.

Since the relative phase information is contained in the one beam exiting the EOS mixing crystal 202, it is not important to have any particular distance from the detector 202 to the polarisation detector 232, as the reference 214 and the reflected terahertz pulse 205 pulses are now encoded in the same polarised pulse 234. Thus, the polarisation sensitive detection mechanism can be placed outside the x and y subsystems as shown in FIG. 6.

Figure 6:
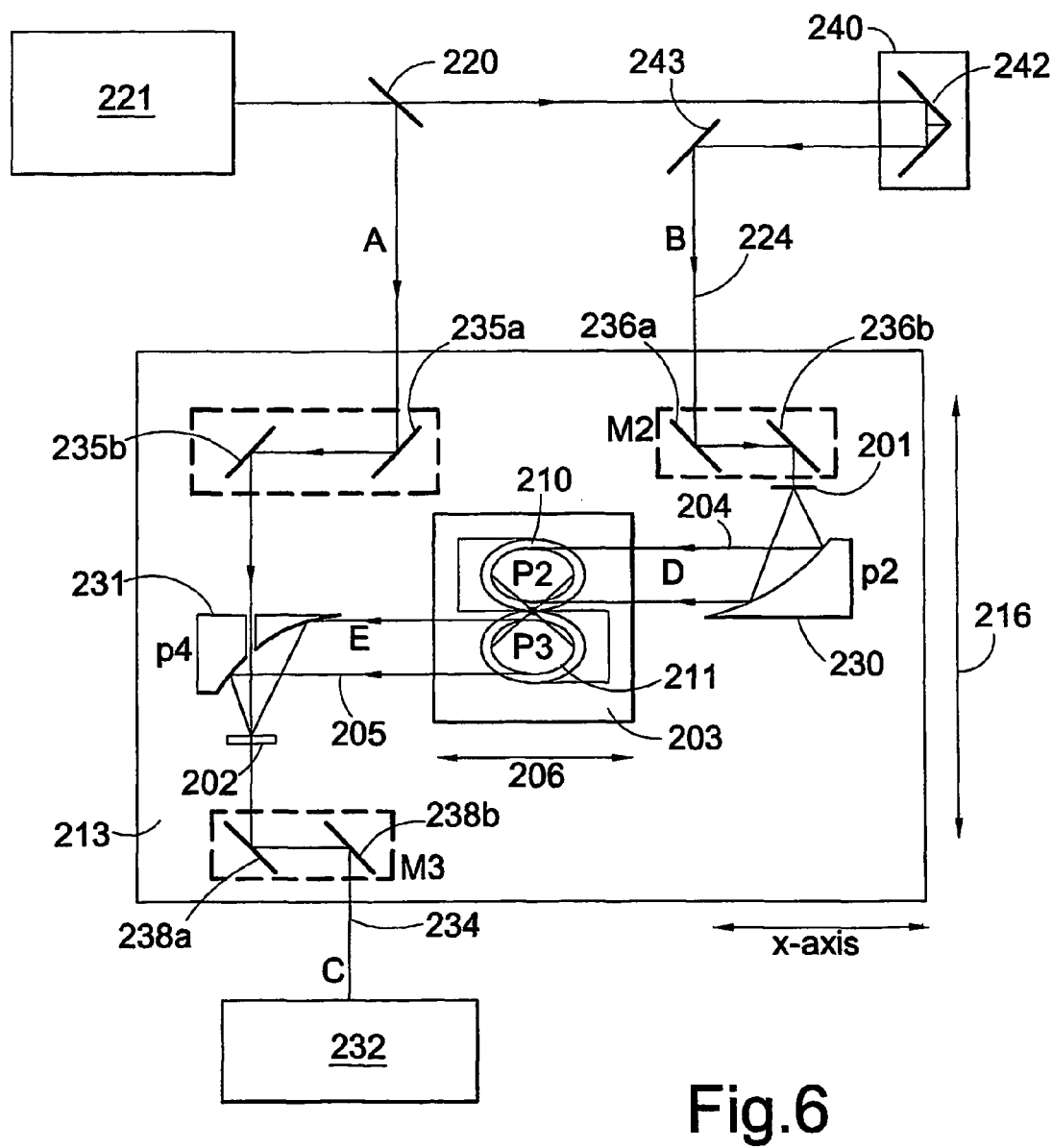
FIG. 6 is a schematic diagram showing an apparatus in accordance with a sixth embodiment of the present invention.

FIG. 6 shows schematically a sixth embodiment of the invention. This embodiment is largely the same as the embodiment shown in FIG. 5, except that the polarisation detector 232 is placed outside the y subsystem 213 rather than inside the y subsystem 213. Here, the polarisation detection system is provided on the opposite side of the y subsystem 213 to the to the source 221. The polarisation detector 232 is fixed with respect to the source 221.

The polarised pulse 234 is manipulated using mirrors 238 so that it is parallel to the y translation axis 216 as it exits the y subsystem 213. This means that the path length of the polarised pulse 234 does not change as the y subsystem 213 moves along the y translation axis 216.

While the apparatus shown in FIGS. 3 to 6 have given examples of a system which can scan the beam in two dimensions, it is readily apparent that these techniques could be extended to three dimensions using the same principles as given above.

Figure 7:
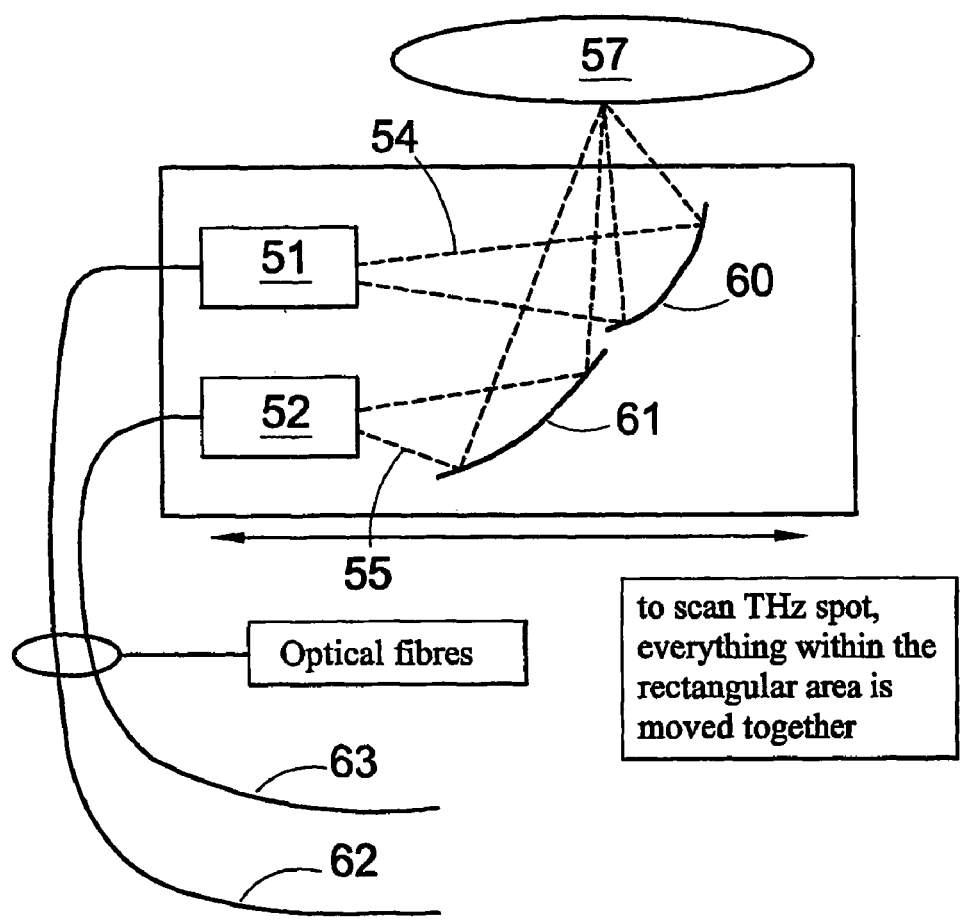
FIG. 7 shows an apparatus in accordance with a farther embodiment of the present invention.
Figure 8:
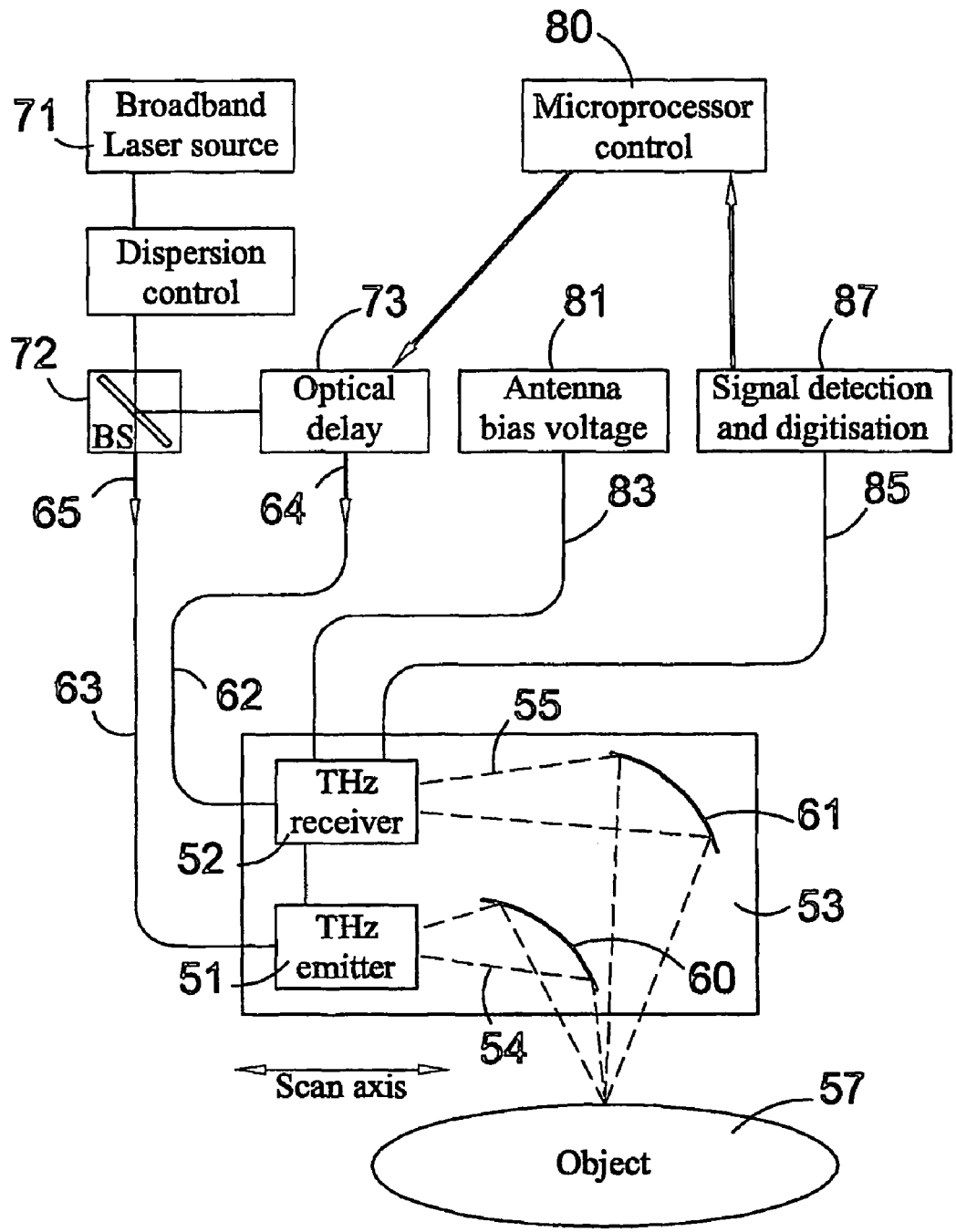
FIG. 8 shows the apparatus of FIG. 7 and its control system.

FIGS. 7 and 8 show schematically a seventh embodiment of the invention. This embodiment includes a subsystem 53, within which an emitter 51 and detector 52 are arranged.

The emitter 51 directs the radiation 54 towards a first parabolic mirror 60 which reflects the radiation to sample 57 under investigation. The radiation 55 reflected from or transmitted through the sample 57 is reflected by a second parabolic mirror 61 to the detector 52. The first and second parabolic mirrors 60, 61 are both within the subsystem 53 (such that they move with subsystem 53) and are fixed relative to the emitter 51 and detector 52.

The emitter 51 comprises a frequency conversion member which emits radiation having the desired frequency, in this example THz radiation, in response to irradiation by an pump beam having a different frequency. In this example, the pump beam is supplied to the emitter using fibre optic cable 62.

The detector operates using a probe beam. The probe beam has a known phase relationship to that of the pump beam. The reference beam is supplied to the detector using fibre optic cable 63.

As the subsystem 53 moves to scan along any axis, the emitter 51 and the detector 52 move with the subsystem 53. The path length of radiation travelling from the emitter 51 to the detector 52 does not change. Neither does the path length of the probe pulse or pump pulse as these are supplied via flexible fibre optic cables 62, 63 which can move with the subsystem 53.

FIG. 8 shows the embodiment of FIG. 7 in more detail. Here, the same source 71 is used as in the third and subsequent embodiments, i.e. a Cr:LiSAF laser. As described in the third and subsequent embodiments, the source 71 produces a pulse which is split into a pump beam 65 and probe beam 64 by beam splitter 72.

The emitter may be a direct emitter of THz radiation which does not require a pump pulse. However in this example, the reference pulse needs to still carry information about the phase of the radiation emitter by the emitter to the detector.

Scanning delay line 73 is provided to cause an oscillating delay in the probe pulse 64. The scanning delay line 73 is connected to microprocessor 80 such that the microprocessor knows the position of the delay line at a point in time in order to analyse the detected radiation.

The pump pulse optic fibre 62 extends between the beam splitter 72 and the frequency conversion device 51. The probe pulse fibre 63 extends between a delay line 73 (from the beam splitter 72) and the detector 52. The each optic fibre 62, 63 is fixed at one end relative to the beam splitter 72, and at the other end relative to the subsystem 53.

The emitter 51 is a photoconductive emitter which emits radiation of the desired frequency in response to irradiation with the pump beam and upon application of a bias across the electrodes. The bias voltage is applied by antenna bias control voltage system 81. The control system 81 is connected to the THz emitter via electrical cable 83.

The THz detector 52 generates a current in response to irradiation by THz radiation in the presence of the probe beam. The measured current is carried via cable 85 to signal detection and digitisation apparatus 87. The signal is then sent to microprocessor 80.

The subsystem 53 can be moved in-any direction relative to the sample 57 because the path length of both source 65 and reference 64 beams are kept constant. This occurs because the optic fibres 62, 63 are of fixed length and are fixed at each end. The relative phase between the source 65 and reference 64 beams is therefore maintained within the system, so that any path difference introduced is caused by the sample 57. This gives the advantage that more complicated optics can be used within the subsystem 53 than parabolic mirrors 60, 61, as they do not have to collimate radiation entering and leaving the subsystem 53, and can be specific to the configuration within the subsystem 53. The subsystem 53 is movable relative to the laser source 71, and the subsystem 53 may be scanned in three dimensions with no extra subsystems.

The data received by the detector can be analysed to find the depth to which the sample pulse travels in to the sample. From this, a partial sample cross-section can be made up by scanning the sample pulse focal point along the translation axis. The delay time of the optical line can be plotted against scanning position.

The embodiments described above may be used in a wide range of imaging applications. As terahertz radiation has no shown detrimental effect on animal or human tissue, it is possible to use it in a wide variety of imaging techniques on various body and other parts, both after removal and in situ. For example, it is possible to obtain results for the thickness of the enamel on a tooth, whether from a human, or other animal. It is also possible to image layers of the skin and other tissues, including the stratum corneum and epidermis.

Many other imaging techniques are possible where the sample is at least partially transparent to terahertz radiation, and surface mapping is possible where the sample is substantially opaque to terahertz radiation.

Figure 9:
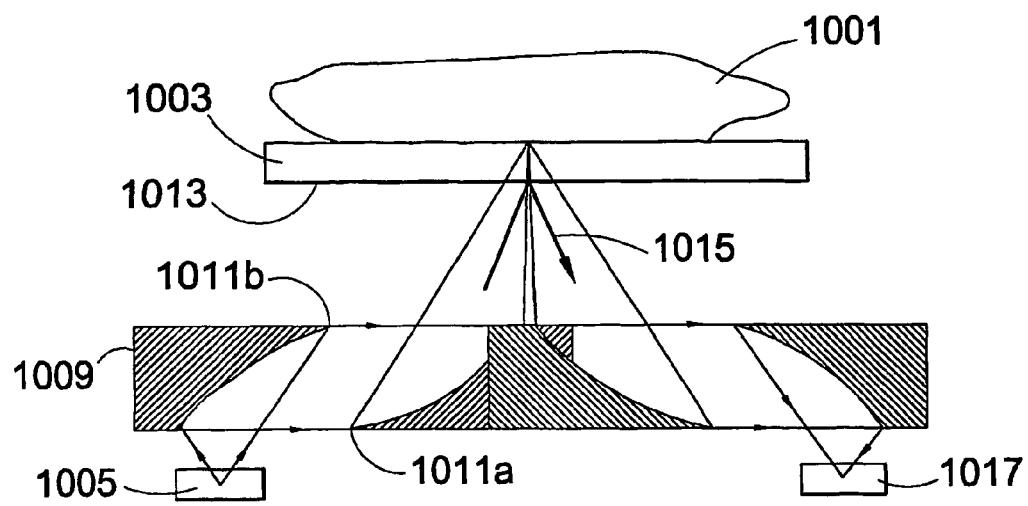
FIG. 9 is a schematic of the principle optics used to image a sample through a window.

In FIG. 9, sample 1001 which is to be imaged is provided adjacent and in contact with window 1003. Window 1003 is positioned such that imaging radiation can only reach sample through window 1003 and radiation reflected from sample 1001 also has to pass through window 1003. The sample imaged using radiation generated by THz emitter 1005 and the radiation reflected from the sample 1001 is detected using THz detector 1007.

Radiation emitted from emitter 1005 is directed to the sample using parabolic mirror assembly 1009. Parabolic mirror assembly 1009 also directs radiation reflected from sample 1001 into THz detector 1007.

THz beams 1011a and 1011b are emitted from THz emitter 1005. Both of these beams 1011a and 1011b are directed through window 1003 onto sample 1001 and reflected back onto parabolic mirror assembly 1009 and into THz detector 1007. However, some of the beams which exit mirror assembly 1009 will not pass through window 1003. Instead, some will be reflected off the underside 1013 of window 1003. The beams 1015 reflected off the underside of window 1013 will also be detected by THz detector 1007. As these beams have not been reflected from sample 1001, these beams contain no information about the sample and should be eliminated.

This problem of extraneous reflections are encountered in many systems as windows are generally desirable. For example, a window may be provided on a sealed case which encloses the imaging system such that atmospheric gases/vapours are excluded from the system. A window can also be used to define the plane of a "soft" sample (e.g. living tissue) or, to protect the THz system from external contamination.

Figure 10:
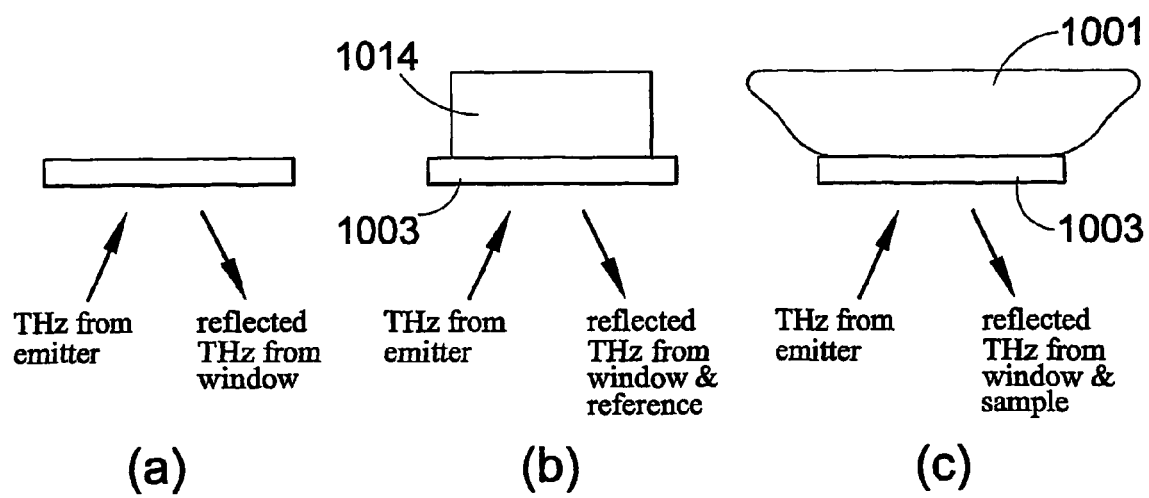
FIGS. 10a, 10b, 10c, show THz radiation being reflected from a window, a reference reflector and window a sample and window respectively.

FIG. 10 illustrates some steps which can be used in order to remove reflections due to the window from the eventual image, so called baseline subtraction.

In FIG. 10a, an image from the THz window 1003 is measured in the absence of sample 1001. Initially, baseline subtraction will be described using just the arrangements of FIGS. 10a and 10c. Then, the use of a reference beam as shown in FIG. 10b will also be explained.

In this specific example, the time domain waveform of the THz reflected from just window 1003 as shown in FIG. 10a is measured. The total reflected THz radiation (reflected from both the sample 1001 and the window 1003) is measured as shown in FIG. 10c.

The baseline signal, that measured in FIG. 10a, is denoted by B(t), in the time domain (where t represents time). A complex Fourier transform is then applied to the signal B(t), to obtain the baseline spectrum B'(v) where (v) represents frequency. The time domain waveform measured with the sample of interest measured in FIG. 10c is denoted by S(t). The complex for Fourier transform of this signal is then taken to obtain the sample spectrum S'(v).

The baseline subtracted waveform in the frequency domain is obtained using the following equation:

$$S'(v) - B'(v)$$

This is then complex Fourier transformed in order to obtain the baseline subtracted waveform or in the time domain.

Alternatively, baseline subtraction can be performed in the time domain.

Figure 11:
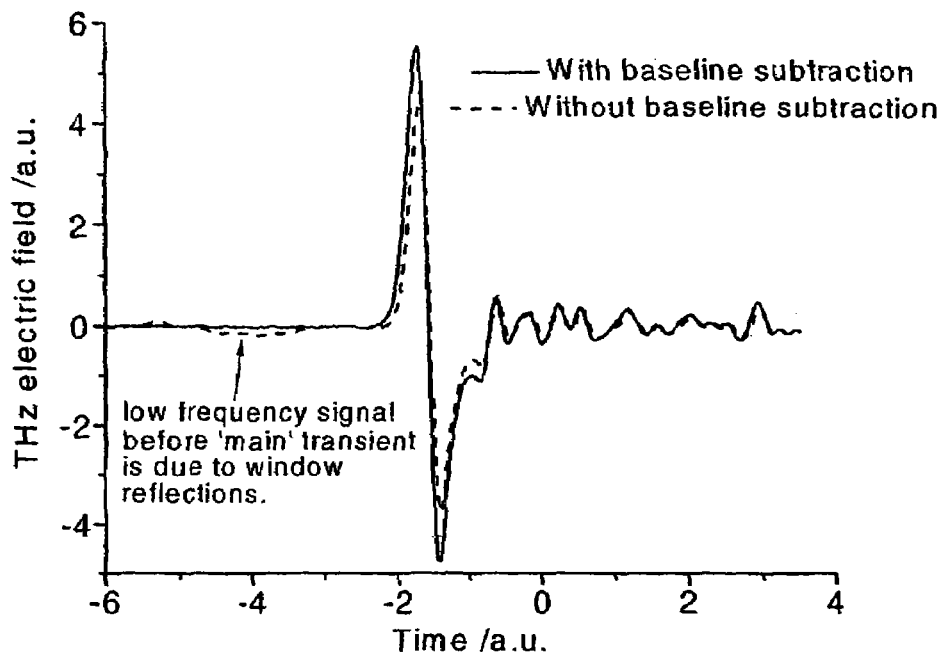
FIG. 11 shows data from a sample measured in accordance with an embodiment of the present invention, the THz electric field (y-axis) is plotted against the time-delay of the signal (the x-axis), the raw data is shown by a dotted line, the solid line shows the same data after baseline subtraction.

FIG. 11 shows a plot of measured THz electric field in arbitrary units against the delay time in arbitrary units with baseline subtraction (shown as a solid line) and without baseline subtraction (shown as a dotted line). The sample image here was a human finger tip. It was imaged using THz radiation having a frequency range of 20 GHz–2.5 THz In general, the image will be further defined by using a reference signal and optionally, a filter function. FIG. 10b shows the use of a reference reflector 1014. The reference reflector 1014 is provided on the opposing side of the window 1003 to the emitter and detector, in the same position as the sample 1001. The reference reflector 1014 is used for spectral comparison. Typically, the reference beam will be obtained using a mirror or other sample with known and constant reflection characteristics.

The time-domain waveform measured using the reference sample is generally represented by R(t). A complex Fourier transform is then applied to this time-domain waveform to obtain the reference spectrum R'(v).

The baseline waveform in the frequency domain is subtracted from both the sample waveform on the reference waveform. The baseline subtracted sample waveform is then divided by the baseline subtracted reference waveform in the frequency in accordance with the following equation:

$$\frac{S'(v) - B'(v)}{R'(v) - B'(v)}$$

The above result is then complex Fourier transformed in order to obtain the final time-domain waveform.

The same reference and baseline waveform can be used as the beam is scanned across the sample as the contribution from the window should not change.

Also, the above procedure could be used where it is necessary to subtract all reflections from other optical surfaces which are present in the sub-system.

The reference and baseline measurements can also be reversed such that the reference waveform is measured from just the window and the baseline is measured with the reference reflector in place.

In general, a filter function will also be used F(t) and is complex Fourier transform will be represented by a F'(v).

A typically preferred filter function is used because the THz pulse system can generate and detect pulses comprising frequencies over some finite range, typically from less than 100 GHz to over 3 THz. There is a high frequency limit above which the THz signal falls below the noise level of the detection system.

Similarly, the THz signal level falls below the noise level at low frequencies. Thus, there is a need to remove the high and low frequency noise. A particularly preferable function for achieving this is:

$$F(t) = \left| \frac{2}{\pi} \left\{ \frac{e^{-2\left(\frac{t}{\alpha}\right)^2}}{\alpha} - \frac{e^{-2\left(\frac{t}{\beta}\right)^2}}{\beta} \right\} \right|$$

The parameters α and β are selected to control the high and low frequency roll-off of the function. α is set approximately the shortest THz pulse length (half cycle) obtainable within the THz system. β is set to be much longer than the THz pulse. In operation, the two parameters are optimised manually by the operator to obtain the best compromise between bandwidth and noise.

As the above function comprises two Gaussian functions with similar areas but opposite signs, the above function ensures that the integral of the filter function for all time is zero.

If the value of β is comparable to or greater than the total time-delay scan range, then an alternative function can be used:

$$F(t) = \left| \frac{2}{\pi} \left\{ \frac{e^{-2\left(\frac{t}{\alpha}\right)^2}}{\alpha} - \frac{1}{T} \right\} \right|$$

where T represents the total range of delay times used i.e. $T = T_{max} - T_{min}$. This ensures that the overall integral from $T_{min}$ to $T_{max}$ is always zero.

Figures 12A, 12B:
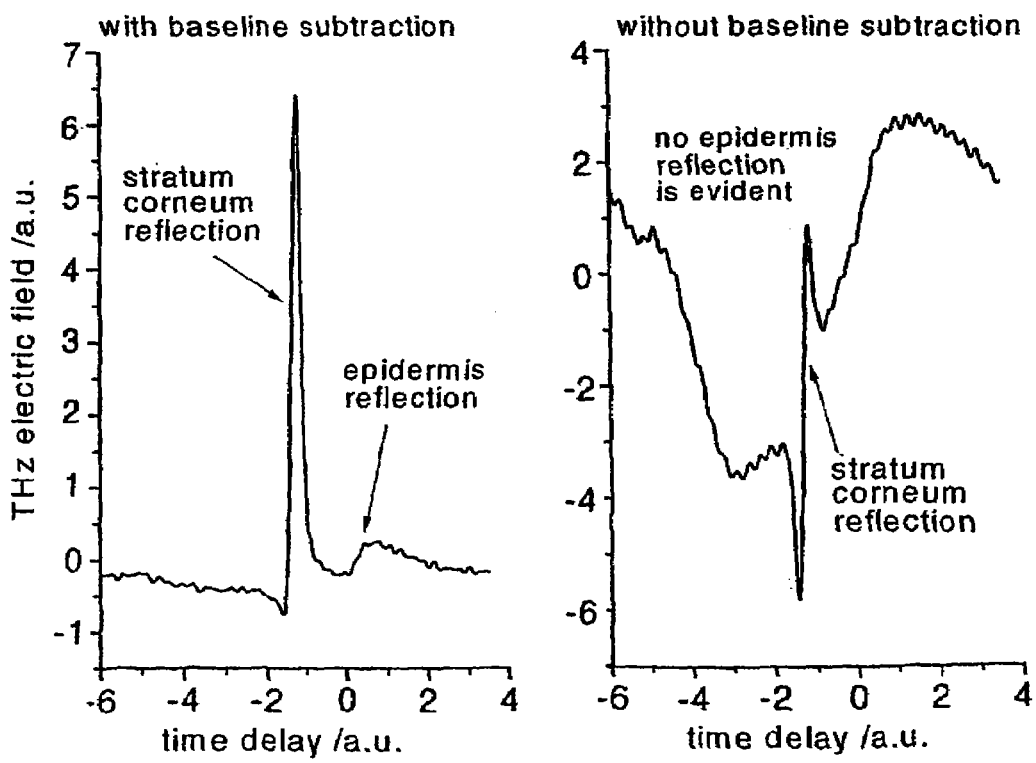
FIG. 12a shows a plot of electric field (y axis) in arbitrary units against time delay (x axis) arbitrary units for a THz scan of skin, the data has been filtered and baseline subtraction has been performed.
FIG. 12b shows the same data without baseline subtraction.

FIG. 12a shows a reflection from skin where the THz electric field is plotted against the time delay in arbitrary units. The data shown in FIG. 12a has been both baseline subtracted, and filtered. The reference beam has also been used.

FIG. 12b shows the same data as FIG. 12a without the baseline subtraction but with the filter function and reference.

Figure 13:
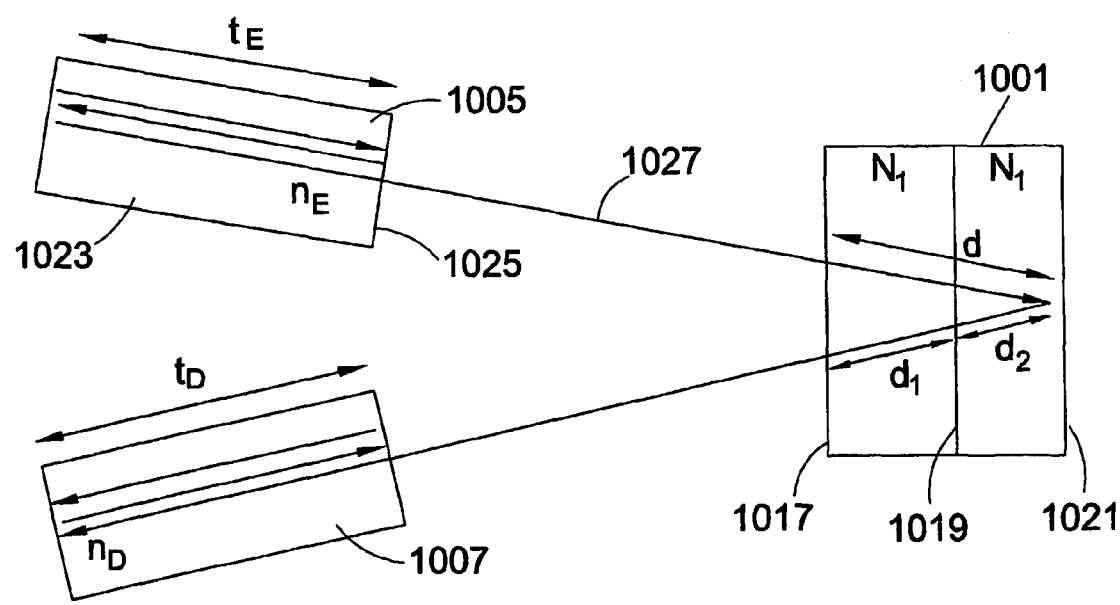
FIG. 13 is a schematic demonstrating the multiple internal reflections which can occur within an emitter during THz reflection imaging.

It is also possible to remove or at least distinguish artefacts due to unwanted reflections by careful choice of the emitter and/or detector thicknesses. In FIG. 13, sample 1001 has a first interface 1017 a first internal interface 1019 and a second internal interface 1021. It is required to find out the position of these three interfaces. However, there is no need to probe the sample deeper than interface 1021. The THz waveform is generated within emitter 1005. In this simplified example, the emitter comprises a single crystal which has a first interface 1023 and a second interface 1025 within the path of the beam. The first and second interfaces 1023 and 1025 are both capable of reflecting the THz radiation. In the ideal case, the THz radiation is generated within the emitter 1005, it follows path 1027 and is reflected off the furthest interface 1021 (amongst other interfaces on sample 1001). The reflected THz signal is then directed into THz detector 1007 for detection. The THz detector 1007 may be a so-called photo-conducting detector where THz radiation 1027 in combination with a probe beam 1029 cause a current to be generated in emitter 1007. Alternatively, it could be a so-called EOS detector where the THz beam 1027 serves to rotate the polarisation of the probe beam 1029. By measuring the change in rotation of the polarisation probe beam 1029, it is possible to measure the THz radiation.

The above is a rather over-simplified example where reflections only occur from the interfaces 1017, 1019 and 1021 in the sample. However, typically, reflections will also occur within the emitter 1005 and detector 1007. In FIG. 13, some of the THz radiation impinging on the second interface 1025 of emitter 1005 is transmitted through the interface towards the sample 1001. However, some of this radiation is reflected back from interface 1025 towards first interface 1023 and then is doubly reflected from interface 1023 through interface 1025 to the sample.

It is desirable to remove the secondary reflection. In this example, the time which the THz radiation takes to be reflected from the first interface 1023 to the second interface 1025 following the path of the THz beam, is longer than the time which it takes the THz radiation to enter sample 1001 through interface 1017 and to reflect from interface 1021.

Thus, the generation crystal is thick enough so that THz pulses reflected off the back of the crystal is measured at optical delay lines greater than that of the sample structure of interest. In FIG. 13, the THz beam radiation travels a distance D through sample 1001 in order to reach interface 1021. On entering the sample, the beam 1007 first travels through the first region which has a refractive index $N_1$ for a distance $D_1$ and then travels through the second region having a refractive index of $N_2$ for a distance $d_2$. The distance which the THz beam travels from the first interface 1023 to the second interface 1025 of the emitter is t. The refractive index of the emitter is $n_e$. For clear observation of the reflection from interface 1021, the following equation must used:

$$t = \frac{N_1 D_1 + N_2 D_2}{n_e}$$

Similarly, the pulse width $t_d$ through the detector having a refractive index of $n_d$ can be calculated in the same manner. The emitter and/or detector may have multiple interfaces. In order to be able to clearly identify the signal due to reflections from each of these multiple interfaces, it is desirable for each of these multiple interfaces to be positioned such that the THz radiation takes longer to travel between two adjacent interfaces than it does to travel through the sample to the interface of interest 1021.

Figure 15:
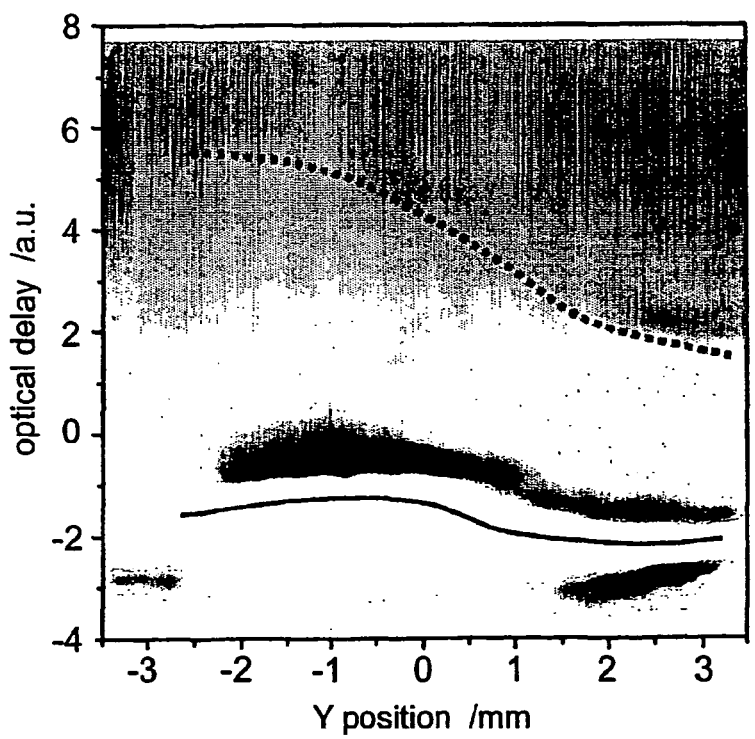
FIG. 15 shows the tooth of FIG. 14 measured using a thicker emitter.

FIG. 15 shows an image of a human tooth which has been measured to a depth of about 1 mm. The generation and detection crystals need to be at least this thickness (in this case, the detection crystal is an ZnTe EOS crystal having a refractive index of 2.6 which is similar to that of the refractive index of dental enamel). The GaAs emitter has a refractive index of 3.6 which is slightly more than that of tooth enamel. Thus, a slightly thinner crystal can be used.

To obtain the shown image, a 0.5 mm emitter crystal was used and a 1 mm detection crystal. In the shown image, the delay time is shown against scanning position along a line along the tooth surface. The amplitude of the signal measured for the delay time is shown on a grey scale where white indicates a strong positive THz field. The signal from the top surface of the sample is shown for low delay times. A ghost image due to reflection within the emitter is shown at a delay time of about 7. Also, a further ghost image which probably arises due to multiple internal reflections within the sample 1001 is also shown.

Figure 14:
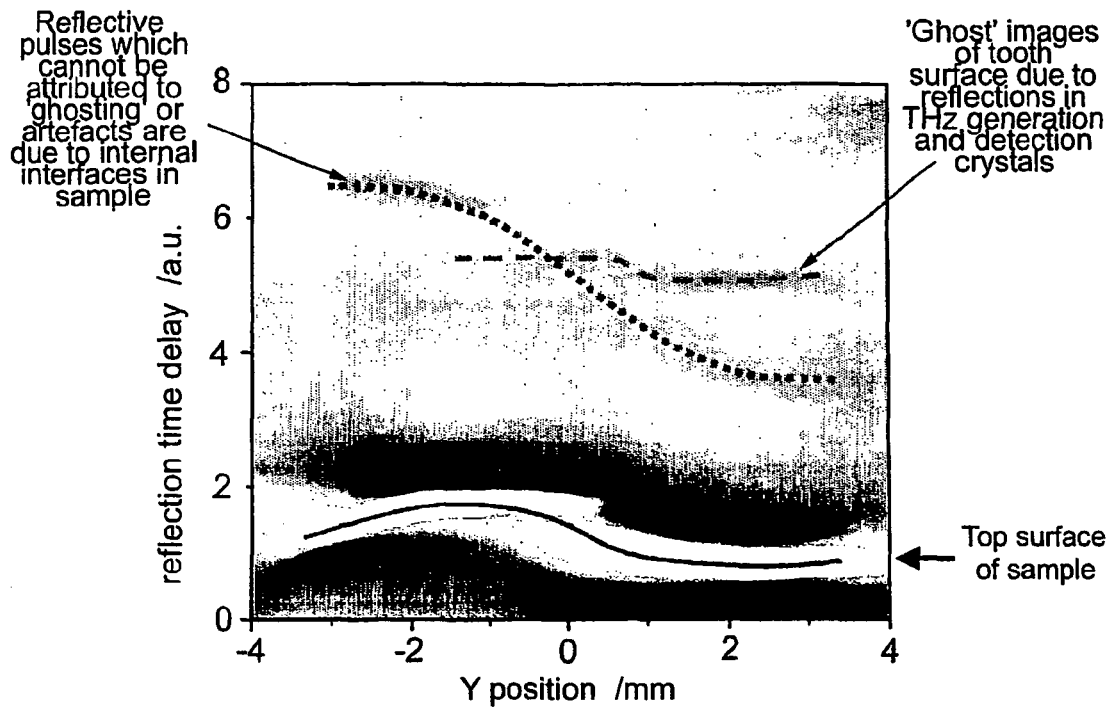
FIG. 14 shows an image of a tooth where ghost images due to reflections within the generation and detection crystals can be seen.

FIG. 15 shows the same sample as FIG. 14 measured with an emitter crystal having a thickness of 1 mm. The signal due to the internal total reflection has disappeared (while the true structural feature of the sample remains).

FIGS. 16a and 16b show visible images of a human tooth. The incisor has been cut in two, FIG. 16a shows an image of the outside of the tooth, whereas FIG. 16b shows an image of the inside of the tooth, a back-side (top rectangle) and a front side (lower rectangle) are identified on FIG. 16b.

FIGS. 17a and 17b show THz images of the back and front sides of the incisor identified in FIG. 16b.

FIG. 18 shows the THz image of the front side of the tooth of FIG. 16b. A reflection artefact due to a 1 mm thick emitter crystal can be seen at the top of the figure. The air/enamel and dentine/air interfaces can also be seen While above embodiments have made use of pulsed radiation, it will be readily appreciated by one skilled in the art that continuous beams of radiation could also be used, in part or in whole to replace the pulses, a pulse being a beam of short duration comprising multiple frequencies.

The present invention has been described above purely by way of example, and modifications can be made within the spirit of the invention. The invention also consists in any individual features described or implicit herein or shown or implicit in the drawings or any combination of any such features or any generalisation of any such features or combination.

Unless the context clearly requires otherwise, throughout the description and the claims, the words "comprise", "comprising", and the like, are to be construed in an inclusive as opposed to an exclusive or exhaustive sense; that is to say, in the sense of "including, but not limited to".

The invention claimed is:

1. An apparatus for investigating a sample, comprising:
a source of a beam of radiation;
a detector for detecting a beam of radiation reflected by or transmitted through the sample;
an optical subsystem for manipulating the beam between the source and detector; and
means for translating the optical subsystem along a first translation axis relative to the sample to scan the beam across the sample; and
means to provide the detector with information concerning the phase of radiation leaving said source,
wherein the beam from the source enters the subsystem on one side of the subsystem in a direction parallel to the first translation axis, and the beam reflected or transmitted exits the subsystem on the opposite side of the subsystem in a direction parallel to the first translation axis.

2. The apparatus of claim 1, further comprising a frequency conversion device between the source and the sample.

3. The apparatus of claim 1, wherein the detector comprises a non-linear optical crystal.

4. The apparatus of claim 1, wherein the detector comprises a photoconductor.

5. The apparatus of claim 1, wherein the sample is irradiated with terahertz frequency radiation.

6. The apparatus of claim 1 wherein the source radiation has a frequency of between $0.1 \times 10^{12}$ Hz and $5 \times 10^{14}$ Hz.

7. The apparatus of claim 1, wherein the incident beam is pulsed.

8. An apparatus for investigating a sample, comprising:
a source of a beam of radiation;
a detector for detecting a beam of radiation reflected by or transmitted through the sample;
an optical subsystem for manipulating the beam between the source and detector; and
means for translating the optical subsystem along a first translation axis relative to the sample to scan the beam across the sample;
wherein the beam from the source enters the subsystem on one side of the subsystem in a direction parallel to the first translation axis, and the beam reflected or transmitted exits the subsystem on the opposite side of the subsystem in a direction parallel to the first translation axis, wherein a reference beam is provided which enters the subsystem parallel to the beam of radiation from the source.

9. The apparatus of claim 8, further comprising a second optical subsystem for manipulating the source and reference beams between the source and the detector, the first optical subsystem being contained within the second optical subsystem.

10. The apparatus of claim 9, further comprising means for translating the second subsystem along a second translation axis relative to the fixed reference point, to scan the source beam across the sample along the second translation axis, wherein source and reference beams each enter the second subsystem in a direction parallel to the second translation axis.

11. The apparatus of claim 8, wherein the reference radiation has a frequency of between $0.1 \times 10^{12}$ Hz and $5 \times 10^{14}$ Hz.

12. The apparatus of claim 8, including a means for implanting a predetermined delay into one of said source and reference beams.

13. An apparatus for investigating a sample, comprising:
a source of a beam of radiation;
a detector for detecting a beam of radiation reflected by or transmitted through the sample;
an optical subsystem for manipulating the beam between the source and detector; and
means for translating the optical subsystem along a first translation axis relative to the sample to scan the beam across the sample;
wherein the beam from the source enters the subsystem on one side of the subsystem in a direction parallel to the first translation axis, and the beam reflected or transmitted exits the subsystem on the opposite side of the subsystem in a direction parallel to the first translation axis, and further comprising a second optical subsystem, for manipulating the source beam between the source and detector, and the first subsystem being contained within the second subsystem.

14. The apparatus of claim 13, further comprising means for translating the second optical subsystem relative to the fixed reference point to scan the source beam across the sample along a second translation axis, wherein the source beam enters the second subsystem in a direction parallel to the direction of translation of the second subsystem.

15. The apparatus of claim 13, wherein the detector is within the second subsystem.

16. The apparatus of claim 13, wherein the detector is outside the second subsystem, and the reference beam and reflected or transmitted beam exit the second subsystem parallel to the direction of translation of the second subsystem.

17. The apparatus of claim 13, wherein the first and second directions of translation are orthogonal.

18. An apparatus for investigating a sample, comprising:
a source of a beam of radiation;
a source of a reference beam;
an optical subsystem for manipulating the source beam;

means for translating the optical subsystem along a first translation axis relative to the sample to scan the beam across the sample; and a detector for detecting the reflected or transmitted beam;

wherein source and reference beams each enter the subsystem in a direction parallel to the first translation axis.

19. The apparatus of claim 18, wherein the detector is within the subsystem.

20. The apparatus of claim 18, wherein the detector is outside the subsystem, and the reference beam and reflected or transmitted beam exit the subsystem parallel to the translation axis of the subsystem.

21. An apparatus for investigating a sample, comprising:

a source of a beam of radiation;

a source of a reference beam;

an optical subsystem for manipulating the beam between the source and a detector; and means for translating the subsystem relative to the sample;

wherein reference beam enters the subsystem through an electromagnetic radiation guide, one end being fixed with respect the source of the reference beam, the other the guide being fixed relative to the subsystem, said reference beam being configured to provide information concerning the phase of radiation leaving said source.

22. The apparatus of claim 21, wherein the source is also outside the subsystem and the source beam enters the subsystem through an electromagnetic radiation guide.

23. The apparatus of claim 21, wherein each electromagnetic radiation guides is an optical fibre.

24. An apparatus for investigating a sample, comprising:

an emitter comprising a frequency conversion member for emitting a beam of THz radiation in response to irradiation by a pump beam of radiation;

a detector configured to detect said beam of THz radiation using a probe beam of radiation;

an optical subsystem comprising said emitter, said detector and means for manipulating the beam between the emitter, a sample and the detector;

the apparatus further comprising means for translating the subsystem relative to the sample such that the emitter and detector move together in a fixed relationship;

a first optical fibre with one end fixed with respect to a source of the pump beam, the other end fixed relative to the subsystem such that the pump beam enters the subsystem through the first optical fibre; and a second optical fibre with one end fixed with respect to a source of the probe beam and the other end being fixed relative to the subsystem such that the probe beam enters the subsystem through the second optical fibre.

25. An apparatus according to claim 24, configured for imaging a sample.

* * * * *